United States Patent
Reddy et al.

(10) Patent No.: US 11,116,966 B2
(45) Date of Patent: Sep. 14, 2021

(54) RETENTION MECHANISM FOR AN IMPLANTABLE LEAD

(71) Applicant: CARDIAC PACEMAKERS, INC., St. Paul, MN (US)

(72) Inventors: G. Shantanu Reddy, Minneapolis, MN (US); Andrew L. De Kock, Ham Lake, MN (US); Benjamin Michael Nitti, Scandia, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 193 days.

(21) Appl. No.: 16/104,242

(22) Filed: Aug. 17, 2018

(65) Prior Publication Data

US 2019/0054289 A1   Feb. 21, 2019

Related U.S. Application Data

(60) Provisional application No. 62/546,867, filed on Aug. 17, 2017.

(51) Int. Cl.
*A61N 1/05*    (2006.01)
*A61N 1/375*   (2006.01)
(Continued)

(52) U.S. Cl.
CPC .......... *A61N 1/057* (2013.01); *A61B 17/3468* (2013.01); *A61N 1/0504* (2013.01); *A61N 1/3752* (2013.01); *A61B 2017/320056* (2013.01); *A61N 1/0558* (2013.01); *A61N 1/0563* (2013.01); *A61N 2001/058* (2013.01)

(58) Field of Classification Search
CPC .... A61N 1/057; A61N 1/3752; A61N 1/0504; A61N 1/0563; A61N 2001/058; A61N 1/0558; A61B 17/3468; A61B 2017/320056
See application file for complete search history.

(56) References Cited

U.S. PATENT DOCUMENTS 4,409,994 A  * 10/1983  Doring ................... A61N 1/057
                                                    607/126
4,716,888 A     1/1988  Wesner
(Continued)

FOREIGN PATENT DOCUMENTS

EP    0085967 A1    8/1983
WO    2012151356 A1  11/2012

OTHER PUBLICATIONS

Darrat et al; "Single Incision Technique for Placement of Subcutaneous Implantable Cardioverter Defibrillators," http://abstractsonline.com/pp8/, accessed May 14, 2018.
(Continued)

*Primary Examiner* — Rex R Holmes
(74) *Attorney, Agent, or Firm* — Seager, Tufte & Wickhem LLP

(57) ABSTRACT

Retention devices for use with an implantable medical device (IMD) are disclosed. An illustrative retention device may comprise an elongate body including a bore configured to receive and substantially surround an implantable lead of the IMD and an outer surface configured to receive a suture. The retention device may also include a securing mechanism configured to push against tissue of the patient.

17 Claims, 25 Drawing Sheets

(51) Int. Cl.
*A61B 17/34* (2006.01)
*A61B 17/32* (2006.01)

(56) References Cited

U.S. PATENT DOCUMENTS

| | | |
|---|---|---|
| 6,647,292 B1 | 11/2003 | Bardy et al. |
| 6,721,597 B1 | 4/2004 | Bardy et al. |
| 7,149,575 B2 | 12/2006 | Ostroff et al. |
| 7,194,302 B2 | 3/2007 | Bardy et al. |
| 7,493,175 B2 | 2/2009 | Cates et al. |
| 7,655,014 B2 | 2/2010 | Ko et al. |
| 8,019,443 B2 | 9/2011 | Schleicher et al. |
| 8,244,377 B1 | 8/2012 | Pianca et al. |
| 8,285,397 B2 | 10/2012 | Grandhe |
| 8,332,043 B1 | 12/2012 | Jaax et al. |
| 9,610,435 B2 | 4/2017 | Schleicher et al. |
| 9,981,121 B2 | 5/2018 | Seifert et al. |
| 2004/0230279 A1 | 11/2004 | Cates et al. |
| 2004/0230282 A1 | 11/2004 | Cates et al. |
| 2006/0095078 A1* | 5/2006 | Tronnes ............ A61N 1/37205 607/2 |
| 2007/0255295 A1 | 11/2007 | Starkebaum et al. |
| 2008/0208247 A1 | 8/2008 | Rutten et al. |
| 2009/0125059 A1 | 5/2009 | Verzal et al. |
| 2009/0210043 A1 | 8/2009 | Reddy |
| 2010/0131036 A1 | 5/2010 | Geistert et al. |
| 2010/0256696 A1* | 10/2010 | Schleicher .......... A61N 1/0558 607/2 |
| 2011/0029057 A1* | 2/2011 | Flach .................. A61N 1/057 607/122 |
| 2011/0054580 A1 | 3/2011 | Desai et al. |
| 2011/0054581 A1 | 3/2011 | Desai et al. |
| 2013/0131767 A1 | 5/2013 | Desai et al. |
| 2014/0144580 A1 | 5/2014 | Desai et al. |
| 2014/0194963 A1 | 7/2014 | Desai et al. |
| 2014/0255298 A1* | 9/2014 | Cole .................... A61K 49/18 424/1.11 |
| 2014/0330248 A1 | 11/2014 | Thompson-Nauman et al. |
| 2014/0330327 A1 | 11/2014 | Thompson-Nauman et al. |
| 2015/0133953 A1* | 5/2015 | Seifert ................ A61N 1/0504 606/129 |
| 2015/0343199 A1 | 12/2015 | Wechter et al. |
| 2015/0352352 A1 | 12/2015 | Soltis et al. |
| 2016/0143643 A1 | 5/2016 | Smith et al. |
| 2016/0339233 A1 | 11/2016 | De Kock et al. |
| 2017/0020551 A1 | 1/2017 | Reddy et al. |
| 2017/0021159 A1 | 1/2017 | Reddy et al. |
| 2017/0095657 A1 | 4/2017 | Reddy et al. |
| 2017/0319845 A1 | 11/2017 | De Kock et al. |
| 2017/0319864 A1 | 11/2017 | De Kock et al. |
| 2018/0036527 A1 | 2/2018 | Reddy et al. |
| 2018/0036547 A1 | 2/2018 | Reddy |
| 2018/0078252 A1 | 3/2018 | Sato |
| 2018/0133458 A1 | 5/2018 | Foster et al. |
| 2018/0133462 A1 | 5/2018 | Reddy |
| 2018/0133463 A1 | 5/2018 | Reddy |
| 2018/0133494 A1 | 5/2018 | Reddy |
| 2018/0169384 A1 | 6/2018 | Reddy et al. |
| 2018/0169425 A1 | 6/2018 | Reddy et al. |
| 2018/0193060 A1 | 7/2018 | Reddy et al. |
| 2018/0214686 A1 | 8/2018 | De Kock et al. |
| 2018/0296824 A1 | 10/2018 | De Kock et al. |
| 2018/0344200 A1 | 12/2018 | Thakur et al. |
| 2018/0344252 A1 | 12/2018 | An et al. |
| 2019/0054290 A1 | 2/2019 | De Kock et al. |
| 2019/0117959 A1 | 4/2019 | Reddy |
| 2019/0151651 A1 | 5/2019 | Reddy et al. |

OTHER PUBLICATIONS

Search Report and Written Opinion dated Sep. 18, 2019 for International Application No. PCT/US2019/028506.

International Search Report and Written Opinion dated Oct. 29, 2019 for International Application No. PCT/US2019/042995.

\* cited by examiner

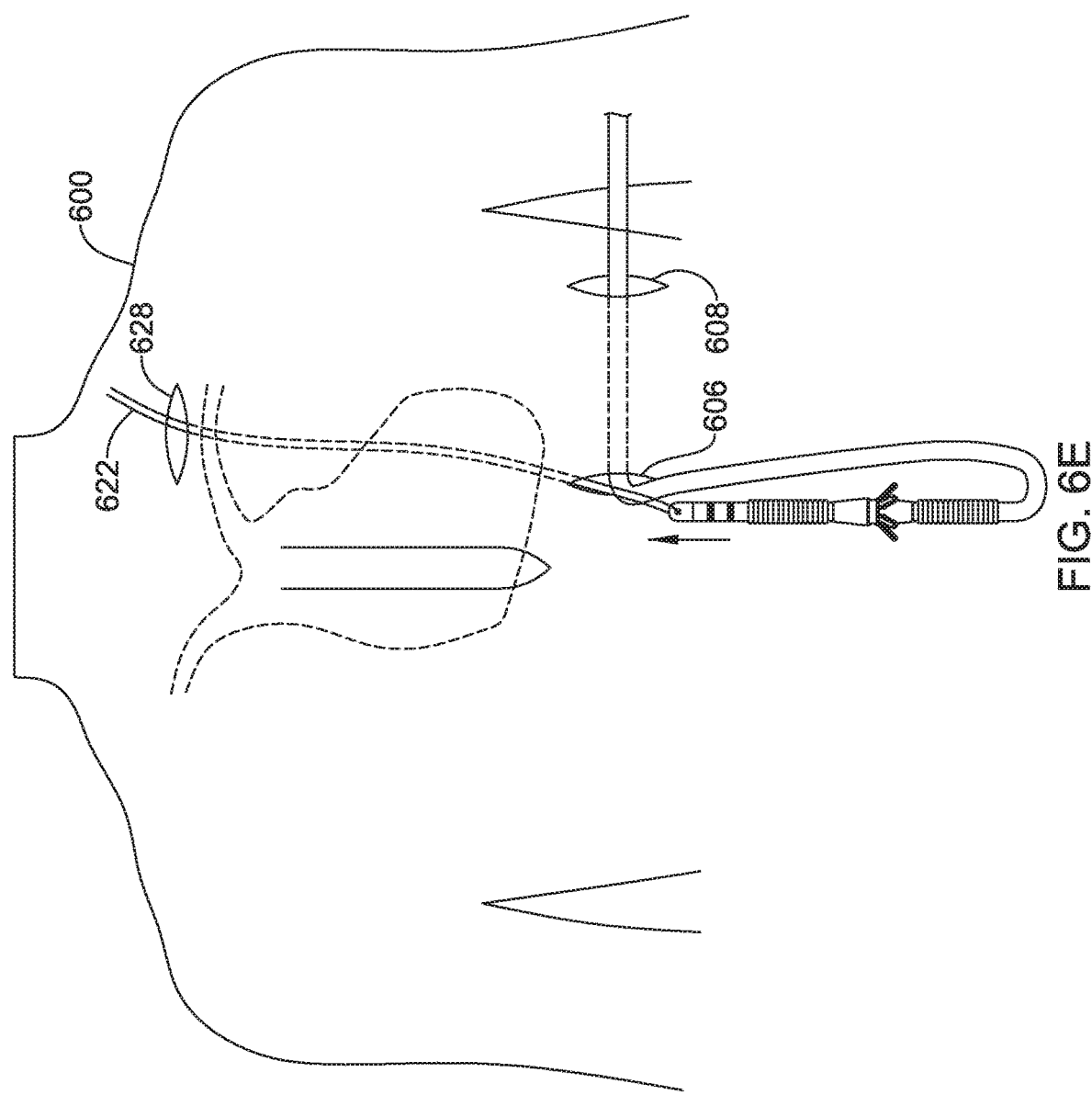

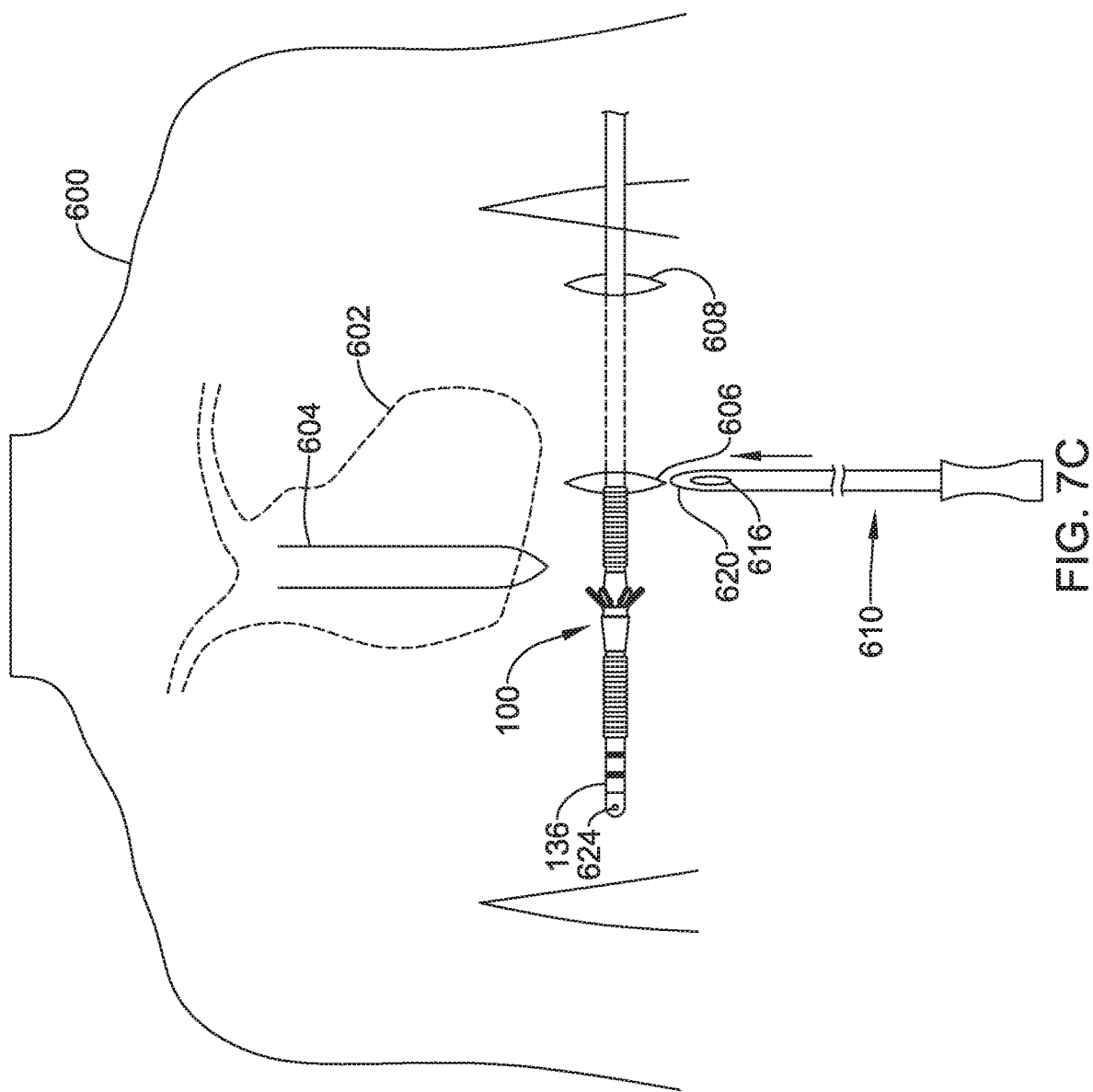

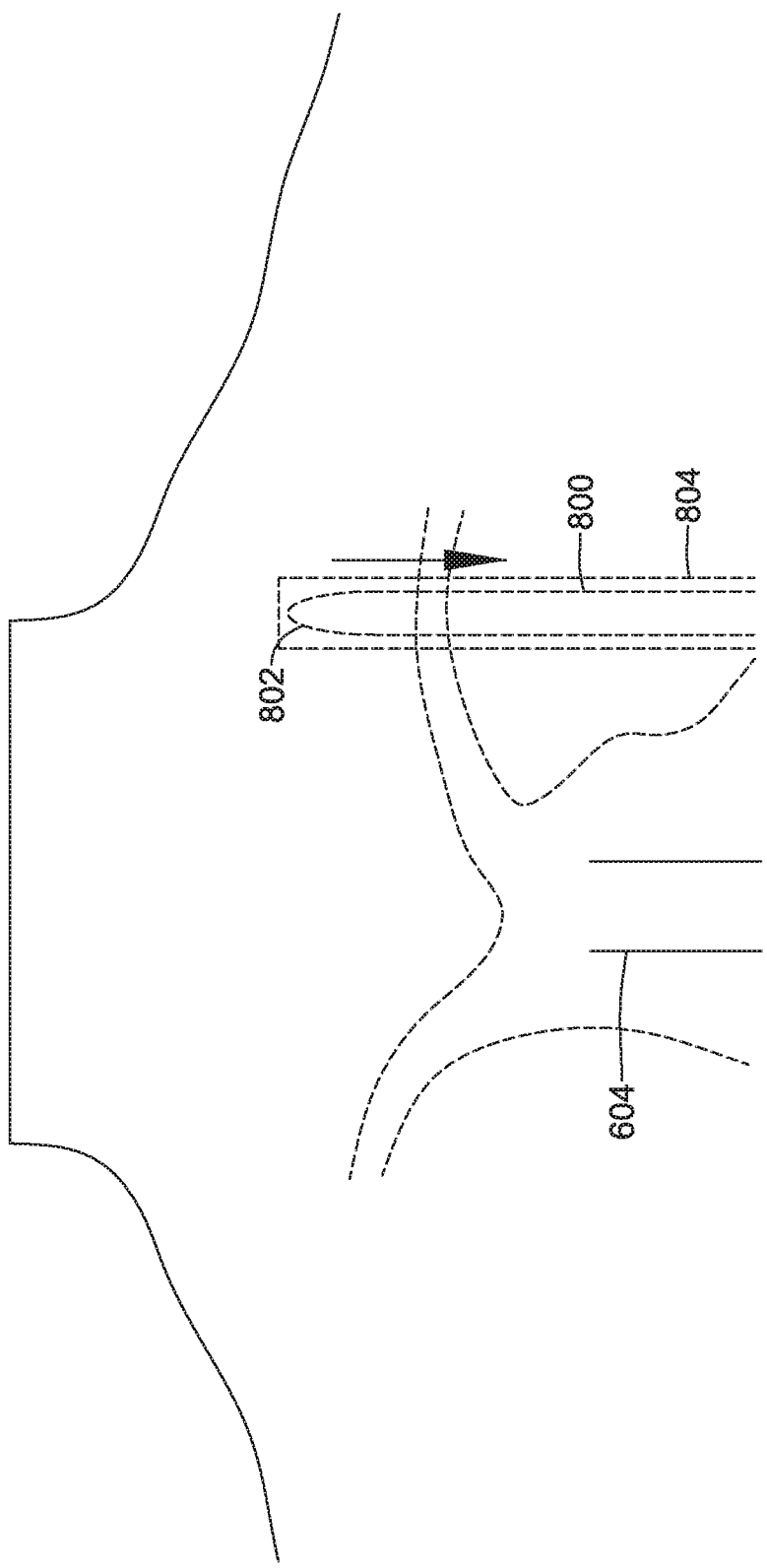

RETENTION MECHANISM FOR AN IMPLANTABLE LEAD

CROSS REFERENCE TO RELATED APPLICATIONS

The present application claims the benefit of and priority to U.S. Provisional Patent Application Ser. No. 62/546,867, filed on Aug. 17, 2017, the disclosure of which is incorporated herein by reference.

BACKGROUND

The subcutaneous implantable cardioverter-defibrillator (S-ICD System) from Boston Scientific is implanted, according to the original FDA labeling thereof, with a subcutaneous lead extending from an implanted pulse generator in an axillary pocket, over the ribs to the xiphoid process, and then superiorly along the left side of the sternum. The implant method as originally approved calls for a suture sleeve fixation near the xiphoid. To affix the suture sleeve at this location to the fascia requires the application of suture loops around the suture sleeve and attachment of the suture to the fascia, through a small 1-2 cm xiphoid incision. There is significant interest in reducing procedure time and simplifying the implant procedure by avoiding such suture steps. Moreover, the multiple incisions called for in the S-ICD System implantation procedure raise risks of infection and leave small but visible scars. This has led to interest in simplification of the implant procedure. New and alternative methods and devices for securing a lead, whether for the S-ICD System or other devices, are desired.

OVERVIEW

A first illustrative, non-limiting example takes the form of a retention device for use with an implantable medical device (IMD) comprising: a elongate body including an outer surface having a recess configured to receive a suture for tying purposes to secure the retention device on a lead; and one or more securing mechanisms each having a first end coupled to the elongate body and a second end configured to push against tissue of the patient.

Additionally or alternatively, the one or more securing mechanisms may comprise a plurality of securing mechanisms radially spaced from one another.

Additionally or alternatively, the one or more securing mechanisms may be made of a flexible material.

Additionally or alternatively, the one or more securing mechanisms may include a first securing mechanism and a second securing mechanism and the first securing mechanism may extend out from the elongate body at a first angle, and the second securing mechanism may extend out from the elongate body at a second angle. In some examples, the first and second angles are equal. In other examples, the first angle is a greater angle than the second angle.

Additionally or alternatively, the one or more securing mechanisms may include a first set of securing mechanisms and a second set of securing mechanisms, the second set of securing mechanisms spaced longitudinally away from the first set of securing mechanisms.

Additionally or alternatively, the first set of securing mechanisms may extend outward from the elongate body in a first direction at a first angle, and the second set of securing mechanisms may extend outward from the elongated body in the first direction at a second angle. In some examples, the first and second angles are equal. In other examples, the first angle is a greater angle than the second angle.

Additionally or alternatively, the first set of securing mechanisms may extend outward from the elongate body in a first direction at a first angle, and the second set of securing mechanisms may extend outward from the elongated body in a second direction at a second angle, wherein the first and second angles are equal and the first and second directions are opposite one another such that the second ends of the first set of securing mechanisms are closer to the second ends of the second set of securing mechanisms than to the first ends of the second set of securing mechanisms.

Additionally or alternatively, the first set of securing mechanisms may extend outward from the elongate body in a first direction at a first angle, and the second set of securing mechanisms may extend outward from the elongated body in a second direction at a second angle, wherein the first and second angles are equal and the first and second directions are opposite one another, and wherein the first ends of the first set of securing mechanisms are closer to the first ends of the second set of securing mechanisms than to the second ends of the second set of securing mechanisms.

Additionally or alternatively, the one or more securing mechanisms may be configured to move from a pre-deployed compressed state to an expanded deployed state.

Additionally or alternatively, the outer surface of the elongate body may have a receiving region of lesser diameter than another region of the outer surface of the elongate body such the when the securing mechanism is in the pre-deployed, compressed state, the receiving region allows the securing mechanism to be compressed therein such that the securing mechanism does not lie outside a largest diameter of the outer surface.

Additionally or alternatively, the outer surface of the elongate body may have a groove such the when the securing mechanism is in the pre-deployed compressed state, the securing mechanism is compressed into the groove such that the securing mechanism does not lie outside a largest diameter of the elongate body.

Additionally or alternatively, at least one securing mechanism may be tine shaped.

Additionally or alternatively, at least one securing mechanism may be hook shaped.

A second illustrative, non-limiting example takes the form of an implantable lead for use with an implantable medical device (IMD), the lead comprising: a lead body having a longitudinal axis extending between a proximal end and a distal end; one or more electrodes disposed on the lead body; one or more conductors coupled to the one or more electrodes; a connector at the proximal end of the lead body for coupling to the IMD, the connector having one or more contacts corresponding to the one or more conductors; and the retention device as in the first illustrative, non-limiting example, or any of the additional or alternative variants thereon.

A third illustrative, non-limiting example takes the form of an implantable medical device system comprising: an implantable device comprising operational circuitry for at least one of analyzing biological signals and delivering therapy to a patient, the operational circuitry disposed in a housing; and an implantable lead as in the second illustrative, non-limiting example, wherein: the implantable pulse generator comprises a port for receiving a connector of the lead assembly; the connector of the lead and the port of the implantable housing are configured to electrically couple the conductor to the operational circuitry; and the operational circuitry is configured to at least deliver therapy using the one or more electrodes or receive a biological signal using the one or more electrodes.

A fourth illustrative, non-limiting example takes the form of a method of implanting an implantable lead in a patient comprising the use of: an implantable lead having a first end for coupling to an implantable medical device and a second end for implantation at a target site in a patient, with a lead body extending therebetween; and a retention device comprising an elongate body having an outer surface with a recess configured to receive a suture to secure the retention device in a desired location on the lead, and one or more securing mechanisms each having a first end coupled to the outer surface of the elongate body and a second end configured to push against tissue of the patient, wherein the one or more securing mechanisms are configured for each of a compressed, pre-deployed state and a deployed state; wherein the method comprises: inserting the implantable lead into a patient with the retention device placed on the lead at a desired location thereon and with a sheath compressing the securing mechanism of the retention device in the pre-deployment state; and at least partly withdrawing the sheath such that the one or more securing mechanisms expand to the deployed state to anchor the implantable lead to tissue of the patient.

Additionally or alternatively, the step of inserting the implantable lead may be performed by making a single incision, advancing an insertion tool having the sheath thereon through the incision and to a selected position in the patient, removing the insertion tool while keeping the sheath in place, and then inserting the implantable lead into the sheath such that the sheath compresses the securing mechanism of the retention device in the pre-deployment state.

Additionally or alternatively, the step of inserting the implantable lead may be performed by: making a first incision and a second incision; making a first tunnel between the first and second incisions; making a second tunnel from the second incision to an end location; passing at least a portion of the lead with the retention device thereon through the first tunnel with the sheath thereover or through the sheath; and passing at least the second end of the lead through the second incision to the end location.

Additionally or alternatively, the step of inserting the implantable lead may be performed such that the retention device is accessible near the second incision, and the method further comprises using a suture to anchor the retention device to the patient using the recess to receive the suture at or near the second incision such that the securing mechanisms and the suture are both used to secure the lead at the selected position.

Additionally or alternatively, the step of inserting the implantable lead may be performed by: making a first incision, a second incision and a third incision; making a first tunnel between the first and second incisions; making a second tunnel between the second and third incisions; passing at least a portion of the lead with the retention device thereon through the first tunnel with the sheath thereover, or through the sheath; and passing at least the second end of the lead through the second incision to the third incision.

Additionally or alternatively, the step of inserting the implantable lead may be performed such that the retention device is accessible near the second incision, and the method further comprises using a suture to anchor the retention device to the patient using the recess to receive the suture at or near the second incision such that the securing mechanisms and the suture are both used to secure the lead at the selected position.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 6A-6F illustrate a three incision method for implanting a lead;
FIGS. 7A-7E illustrate a two incision method for implanting a lead;
FIGS. 8A-8C illustrate a single incision method for implanting a lead.

DETAILED DESCRIPTION

The following detailed description should be read with reference to the drawings. The drawings, which are not necessarily to scale, depict illustrative embodiments and are not intended to limit the scope of the invention. Any references to other patents or patent applications are intended as illustrative of useful methods or devices and are not intended to foreclose suitable alternatives. In the methods shown below, structures may be beneath the skin and over the ribcage of the patient, though such elements are not always shown in phantom. Some examples may place devices in the abdomen, again making use of suturing techniques that anchor to the fascia.

The words "proximal" and "distal" are used herein to differentiate the ends of devices. No specific anatomical significance is intended. For example, the distal end of a lead is not necessarily anatomically distal relative to the proximal end of the lead; anatomic distal and proximal terminology will be determined by the final implantation location(s).

Figure 1A:
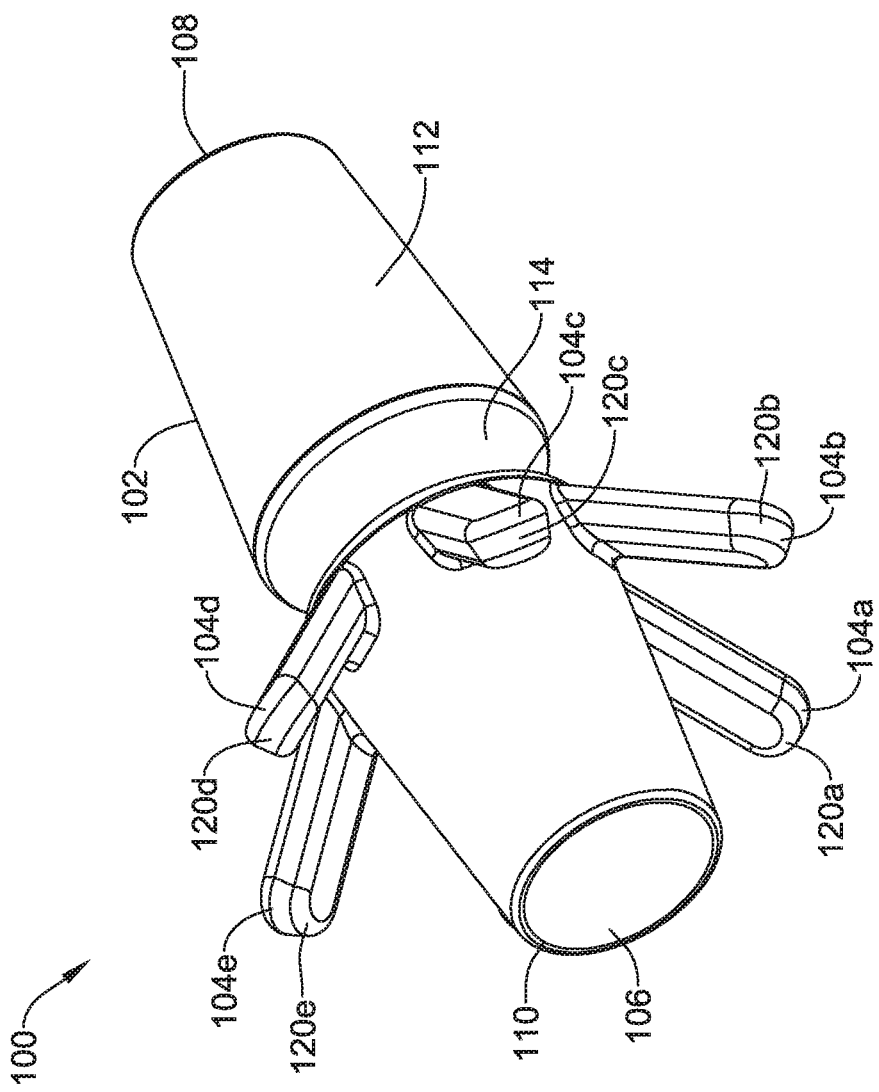
FIG. 1A shows a first exemplary retention device.

FIG. 1A shows an exemplary retention device 100. As shown, the retention device may include an elongate body 102 and securing mechanisms 104A-104E. According to various embodiments, the elongate body 102 may have a bore 106 that extends from an open distal end 108 to an open proximal end 110. In an example, the bore 106 is dimensioned to receive a portion of an implantable lead therein. The elongate body 102 may be formed from any material suitable for chronic implantation in patients.

The elongate body 102 may also include one or more recesses 114 on an outer surface 112 that can receive a suture to assist in securing the retention device 100 at a desired location on the lead. For example, tightening the suture onto the elongate body 102 while in a recess 114 can reduce the diameter of the bore 106 to secure the retention device 100 onto a lead. In some examples, a suture may also be used to secure the retention device 100 at a selected position in the patient. In other examples, particularly those that are adapted to place the device 100 without suturing it to the patient's tissue, the securing mechanisms 104A-104E are solely relied upon to anchor the device.

According to various embodiments, the securing mechanisms 104A-104E may be located on the elongate body 102 and may be configured to push against tissue of the patient when the retention device 100 is implanted inside the patient. In some cases, the securing mechanisms 104A-104E may be flaps that are a formed, single-piece, with the elongate body 102. In some cases, the securing mechanisms 104A-104E may have first ends attached to the elongate body 102 in any suitable manner, which may include hinges, screws, pins and/or any other suitable fastener. In some cases, the first ends may be molded to the elongate body 102 so that joints are formed. In some cases, the joints may be configured to pivot so that second ends 120A-120E of the securing mechanisms 104A-104E move, retract, or compress towards the elongate body 102 to a compressed state. In some cases, the joints may be further configured to pivot so that the second ends 120A-120F move, swing, or extend away from the elongate body 102 to an extended state. Rather than a defined joint, the securing mechanisms may simply flex toward and away from the elongate body.

As shown in FIG. 1A, the outer surface 112 of the retention device 100 may have a diameter that varies along the elongate body 102. In some examples, the outer surface 112 may taper, incline, or slope, to a smaller diameter from a larger diameter at the location where the first ends of the securing mechanisms 104A-104E attach to the retention device 100. As such, when the securing mechanisms 104A-104E are in the compressed state, the second ends 120A-120E of the securing mechanisms may be located adjacent to the smaller diameter portion, so that the retention device may present an outer diameter that does not change significantly along its length. When disposed in a sheath, the outer diameter of the sheath may be generally smooth as a result, avoiding unnecessary trauma to the patient during insertion.

In various embodiments, the securing mechanisms 104A-104E may be comprised of the same materials as the elongate body 102. However, in some embodiments, the securing mechanisms 104A-104E may be comprised of different materials than the elongate body 102. In certain embodiments, the securing mechanisms 104A-104E may be comprised of a different, stiffer, material than the elongate body 102. Alternatively, the securing mechanisms may be softer than the elongate body 102. In some examples the securing mechanisms may be formed of silicone while a different polymer of stiffer or harder character is used for the elongate body 102. In other examples, the securing mechanisms may be coated or uncoated nitinol or other metal, making them generally stiffer than the elongate body. In some cases, the securing mechanisms 104A-104E may be radiopaque.

According to various embodiments, the securing mechanisms 104A-104E may be arranged to enable the retention device 100 to be collapsed by a sheath to a pre-deployed state. When the retention device 100 is in a selected position or configuration during implantation in the patient, the sheath may be removed. Upon removal of the sheath, the securing mechanisms 104A-104E may expand to engage, push against, and/or anchor the retention device 100 in a desired location such as the subcutaneous tissue of a patient.

In one example, a shape memory material is used for the securing mechanisms 104A-104E, such that a compressed state may be achieved with little tension exerted by the securing mechanisms until body temperature is reached during implantation. Once implanted and with the insertion sheath removed, the shape memory material can then cause the securing mechanisms to spring outward, anchoring to the surrounding tissue.

In various embodiments, the securing mechanisms 104A-104E may be tine shaped, hook shaped, fan shaped, a combination thereof, etc. Furthermore, the securing mechanisms 104A-104E may have rounded second ends 120A-120E to encourage tissue anchoring without piercing through the skin or other sensitive anatomical structures. In other embodiments, the second ends 120A-120E may be square, pointed, convex, barbed, etc.

In certain embodiments, as depicted in FIG. 1A, there may be several securing mechanisms 104A-104E that are radially spaced from one another around the elongate body 102. In some cases, the securing mechanisms 104A-104E may be limited to one side of the elongate body 102. In some instances, there may be a single securing mechanism 104A.

In some examples, the shapes of the securing mechanisms 104A-104E may vary from one another. For example, different ones of the securing mechanisms 104A-104E may have different lengths or widths from one another. Some may be tapered, barbed, and/or pointed, while others may have a different shape such as being rounded. In some examples such as that shown, the securing mechanisms 104A-104E may all have the same width, length and shape.

In some examples, the securing mechanisms 104A-104E may be attached to the elongate body 102 such that the securing mechanisms 104A-104E have a desired degree of angular separation with the elongate body 102 in an uncompressed or relaxed state. For example, the securing mechanisms 104A-104E may be configured so that there is a 45° angle of separation between the securing mechanisms 104A-104E and the elongate body 102. In some cases, the angle of separation may be 15°, 30°, 60°, 90°, etc. In some cases, the angles of separation may be substantially the same or equal across each of the securing mechanisms 104A-104E. In some cases, the angles of separation may not be the same or equal to one another. Thus, while the examples shown generally have sets of securing mechanisms 104A-104E that are symmetrically placed about the circumference of the retention device 100 with similar angular and shape characteristics, this need not be the case and different ones of the securing mechanisms 104A-104E may be differently oriented, sized or shaped, if desired. In addition, different ones of the securing mechanisms 104A-104E may have differing material properties, if desired. The various noted variations in shape, quantity, distribution, size, orientation, angular configuration, etc. may be incorporated in any of the following illustrative examples.

Figure 1B:
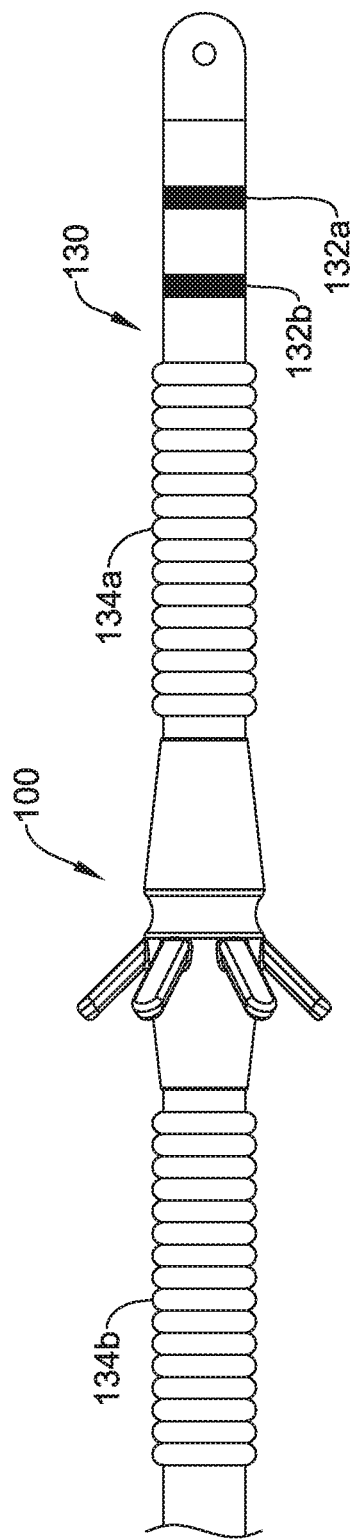
FIG. 1B shows the first exemplary retention device coupled to a lead.

FIG. 1B shows the retention device 100 coupled to an illustrative lead 130. As shown, the bore may receive and substantially surround the lead 130. The lead 130 may include ring electrodes illustrated at 132A, 132B as well as coil electrodes 134A, 134B, though other electrode types and quantities may be used. For example, a directional electrode array may be used. The lead 130 may be manufactured of any suitable material and by any suitable manner. As noted above, a suture may be applied to the retention device 100 at the groove thereof to secure it to the lead 130 prior to or during implantation.

Figure 2A:
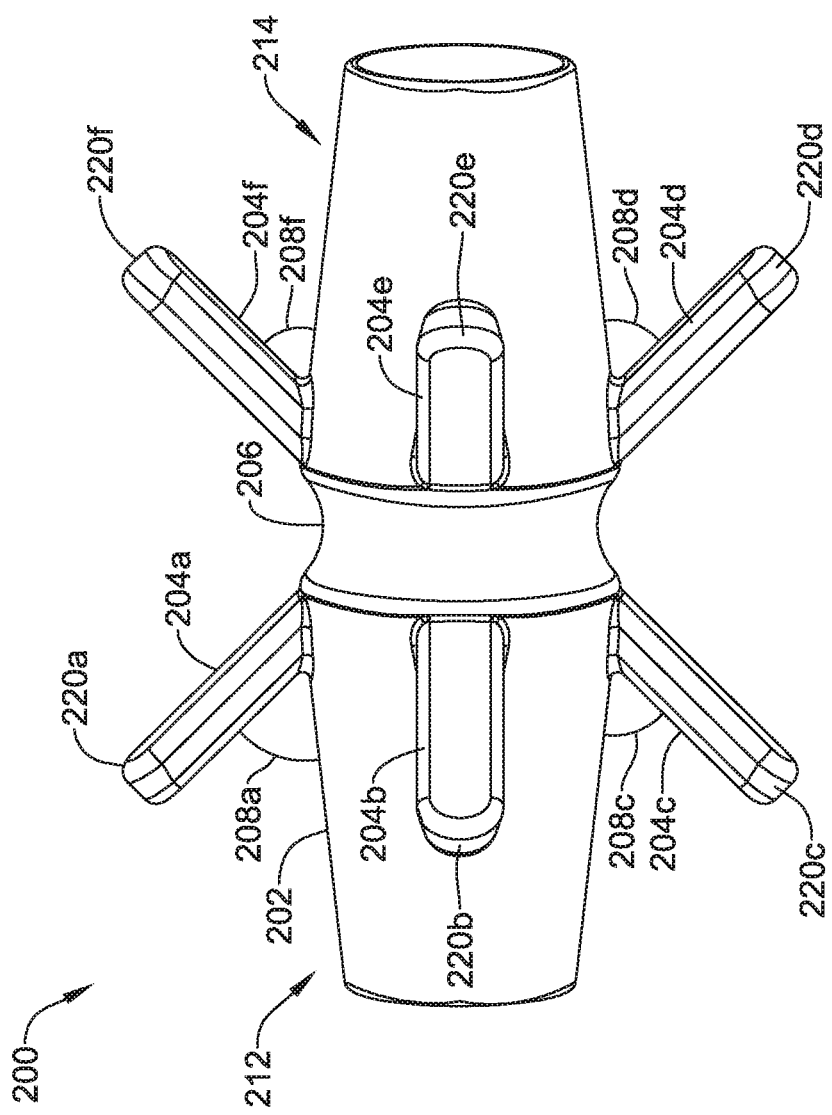
FIG. 2A shows a second exemplary retention device.

FIG. 2A shows a second exemplary retention device 200. As shown, the retention device 200 may include a body 202, securing mechanisms 204A-204F, and a recess 206. The materials comprising the retention device 200 and the operation of the retention device 200 may be similar to that of the retention device 100 described in regard to FIG. 1A in several respects such as material used and overall structure. However, as can be seen in this embodiment, the securing mechanisms 204A-204F are arranged such that a first set of securing mechanisms 204A-204C are radially spaced from one another and around the elongate body 202 at a first location, and a second set of securing mechanisms 204D-204F are spaced longitudinally away from the first set 204A-204C and are radially spaced from one another around the elongate body 202.

As can be seen, the securing mechanisms 204D-204F are orientated in a mirror configuration of the securing mechanisms 204A-204C. That is, the angle relative to the elongate body 202 is the same for each of the sets of securing mechanisms, but the two sets are oriented in opposing direction.

In this example, an outer surface 210 may have two tapered portions 212 and 214. The first ends 216A-216C of the securing mechanisms 204A-204C may be located adjacent to a larger diameter of the tapered portion 212. As such, when the securing mechanisms 204A-204C are in the compressed state, second ends 220A-220C may be located adjacent to a smaller diameter of the tapered portion 212. Similarly, first ends 216D-216F of the securing mechanisms 204D-204F may be located adjacent to a larger diameter of the tapered portion 214. As such, when both sets of securing mechanisms are in the compressed state, the second or free ends thereof are located adjacent to a smaller diameter of the tapered portions 212, 214. Accordingly, when in the compressed state, the securing mechanisms 204A-204F may not lie outside the large diameters of the tapered portions 212 and 214. This may be beneficial to present a smoother outer contour when within an introducer sheath.

Figure 2B:
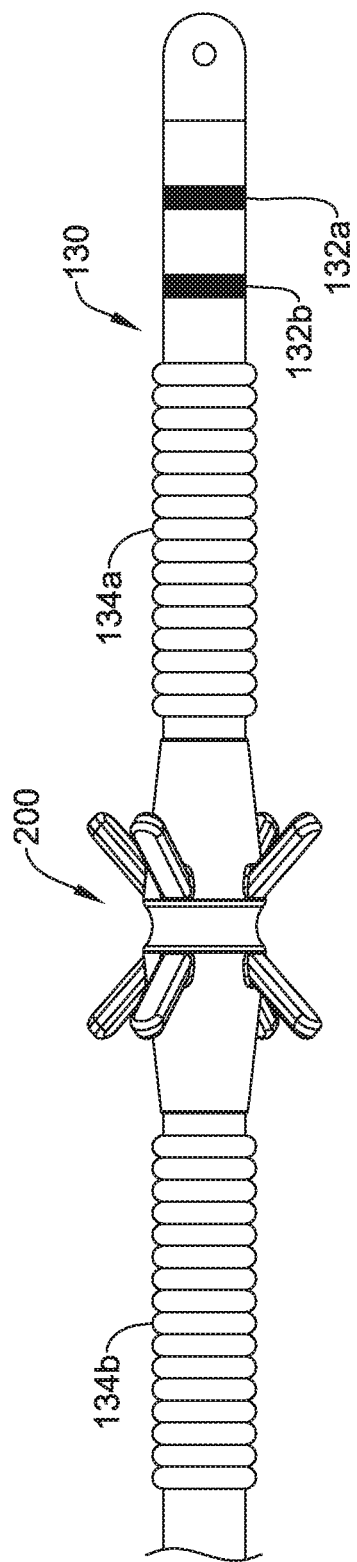
FIG. 2B shows the second exemplary retention device coupled to a lead.

FIG. 2B shows the retention device 200 coupled to an illustrative lead structure 130. The configuration and operation of the lead 130 with the retention device 200 may be similar to the lead 130 with the retention device 100 described in regard to FIG. 1B.

Figure 3A:
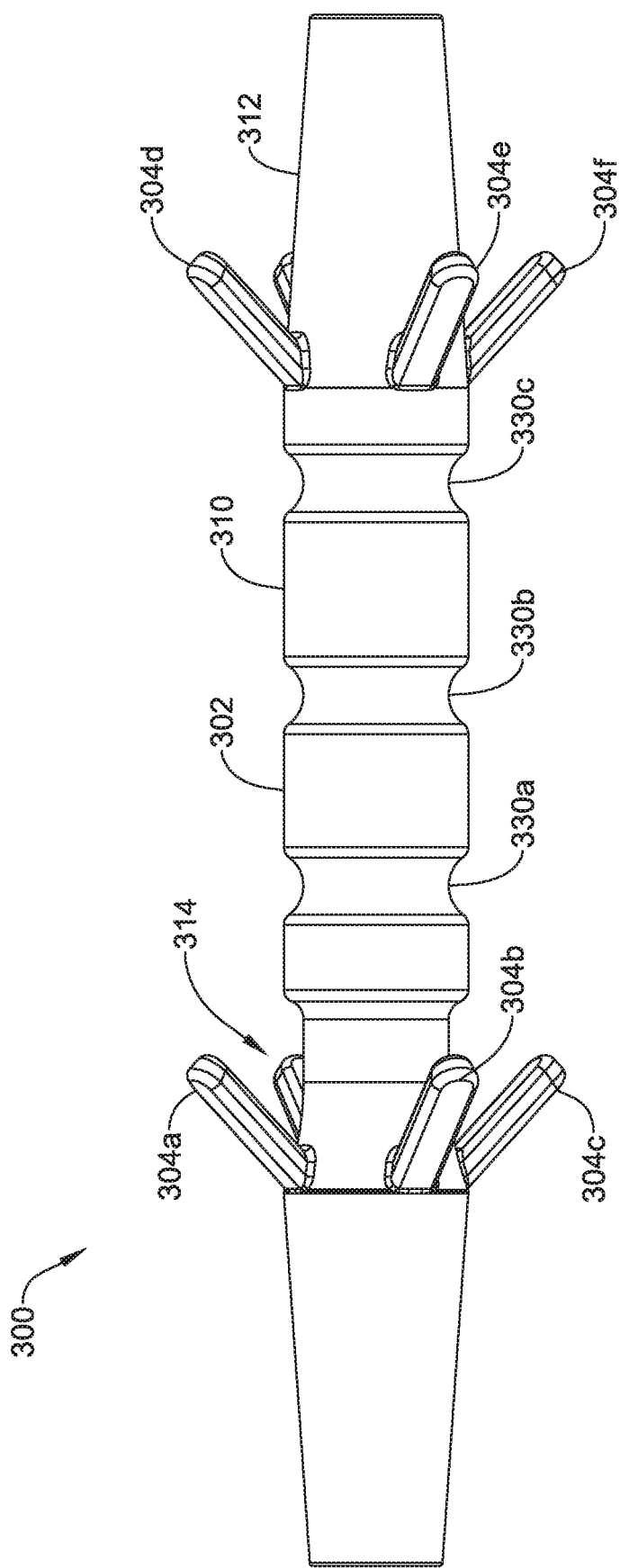
FIG. 3A shows a third exemplary retention device.

FIG. 3A shows a third exemplary retention device 300. In this example, there are two sets of securing mechanisms 304A-304F, all of which are oriented in the same direction on the device 300. In addition, a plurality of recesses are provided as shown at 330A-330C. The inclusion of several such recesses 330A-330C may allow more structural flexibility or greater force to be applied to hold the retention device 300 on a lead. In some examples, the inclusion of several recesses 330A-330C offers a wider range of options for positional alignment of an implanted lead or electrode to patient anatomy. It is expected that 1, 2 or all 3 of the recesses 330A-330C may be used, and a physician may choose which to use based on preference or the needs of a particular implant. Again tapered sections 312 are provided on each end of the lead, as well as a recess shown at 314, to allow the securing mechanisms to be folded down to the compressed state for introduction into a patient. That is, the tapered section 312 may be designed, such that when the tines are folded down they do not increase the outer diameter of the retention device 300. In alternative examples, rather than a taper or in addition to a taper, a longitudinally extending groove may be provided to receive the securing mechanisms (and the same may be said for each of the above and below examples of retention devices).

Figure 3B:
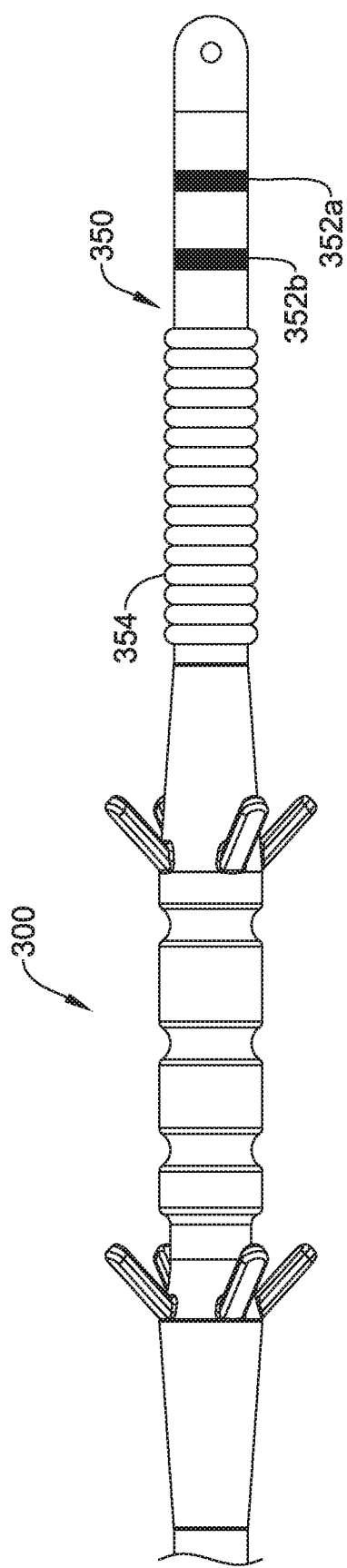
FIG. 3B shows the third exemplary retention device coupled to a lead.

FIG. 3B shows the retention device 300 coupled to an illustrative lead structure 350. The lead 350 may include ring electrodes illustrated at 352A, 352B as well as coil electrode 354. The configuration and operation of the lead 350 with the retention device 300 may be similar to the lead 130 with the retention device 100 described in regard to FIG. 1B.

Figure 4A:
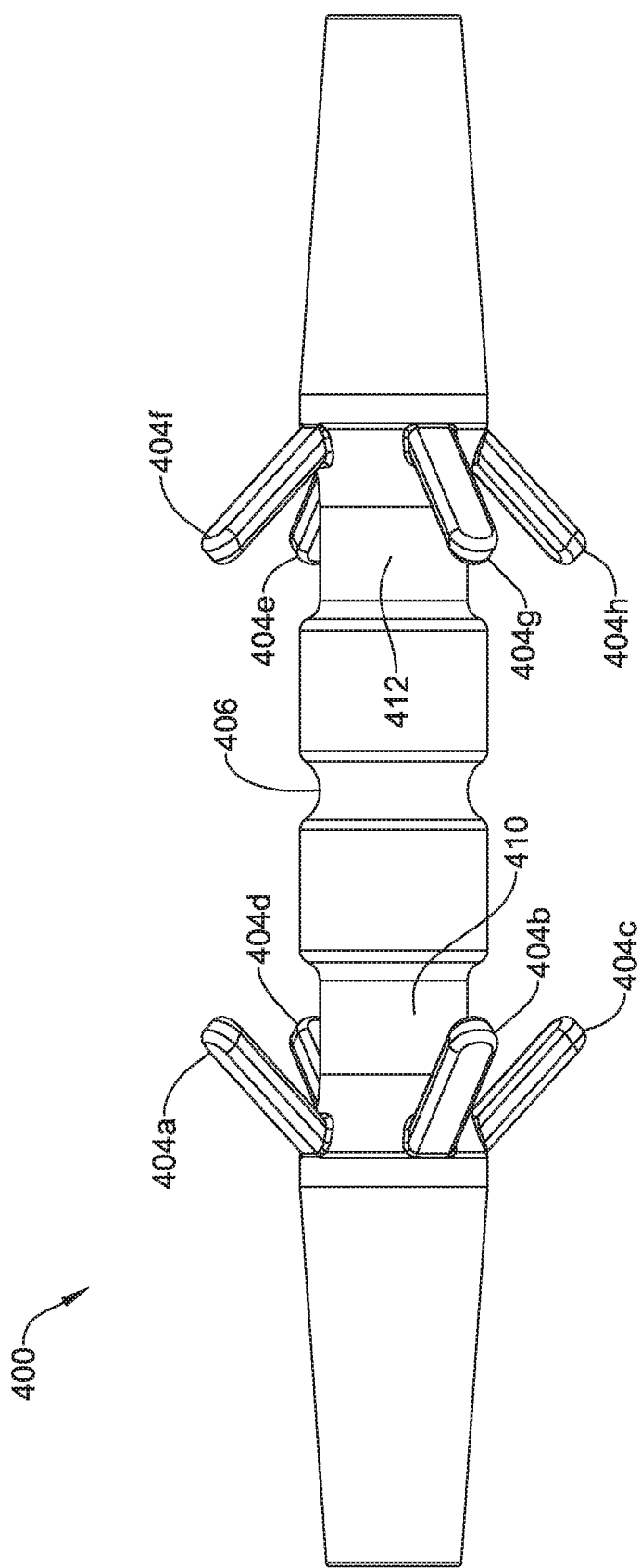
FIG. 4A shows a fourth exemplary retention device.

FIG. 4A shows a fourth exemplary retention device 400. The materials comprising the retention device 400 and the operation of the retention device 400 may be similar to that of the retention devices 100 and 200, described above. The retention device 400 may include two sets of securing mechanisms 404A-404D and 404E-404H radially spaced from one another and orientated in a mirror configuration of one another, similar to securing mechanisms 204A-204C and 204D-204F of the retention device 200. The retention device 400 may also include a recess 406 that may be configured to operate similar to recess 114 of the retention device 100. The retention device 400 may also include grooves 410 and 412 that are configured to allow the securing mechanisms 404A-404D and 404E-404H to retract inside, similar to the groove 332 of the retention device 300, described in regard to FIG. 3A. A physician may also choose to use the grooves 410, 412 as locations to apply a suture for attaching to tissue or for securing the retention device 400 to a lead.

Figure 4B:
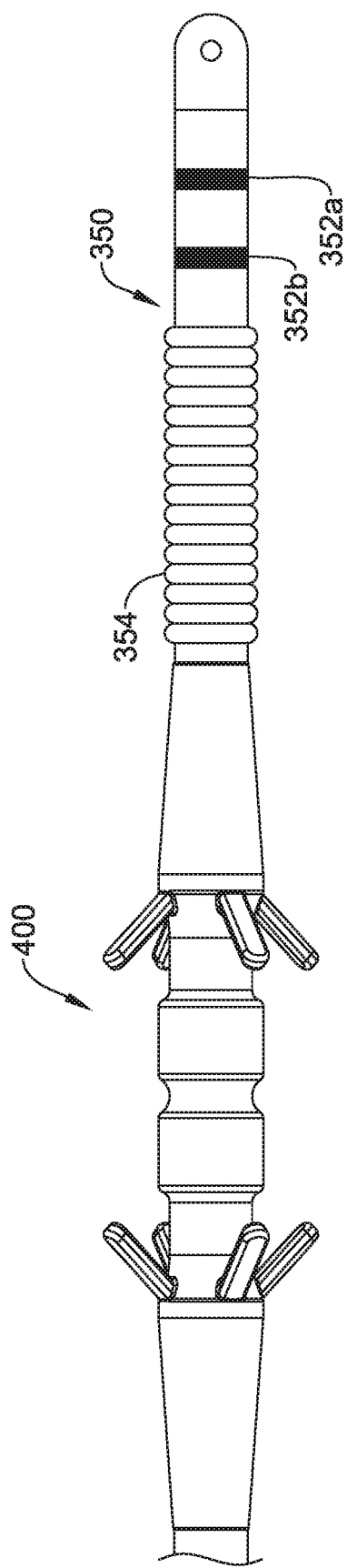
FIG. 4B shows the fourth exemplary retention device coupled to a lead.

FIG. 4B shows the retention device 400 coupled to the illustrative lead structure 350. The configuration and operation of the lead 350 with the retention device 400 may be similar to the lead 130 with the retention device 100, described in regard to FIG. 1B.

Figure 5A:
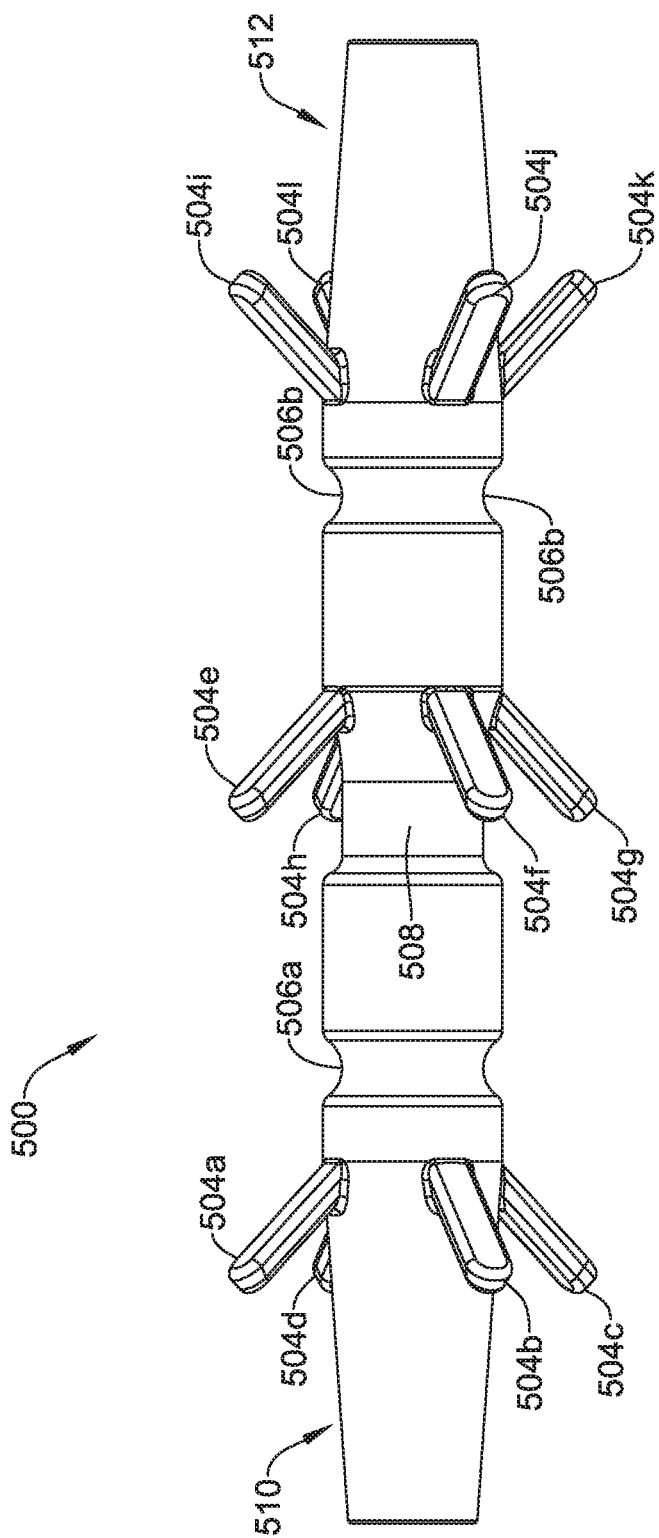
FIG. 5A shows a fifth exemplary retention device.

FIG. 5A shows a fifth exemplary retention device 500. The materials comprising the retention device 500 and the operation of the retention device 500 may be similar to that of the retention devices 100 and 200, described above. The retention device 500 may include three sets of securing mechanisms 504A-504D, 504E-504H, 504I-504L radially spaced from one another. In this embodiment, securing mechanisms 504A-504D and 504E-504H are orientated in a symmetric configuration and securing mechanisms 504I-504L are orientated in a mirror configuration of securing mechanism 504A-504D and 504E-504H. The retention device 500 may also include a recesses 506A-506B that may be configured to operate similar to recess 114 of the retention device 100. The retention device 500 may also include a groove 508 configured to allow the securing mechanisms 504E-504H to retract inside, similar to the groove 332 of the retention device 300, described above. In addition, tapered portion 510 may allow the securing mechanisms 504A-504D to retract back such that, when in a compressed state, the securing mechanisms 504A-504D may not lie outside a largest diameter of the tapered portion 510. Similarly, tapered portion 512 may allow the securing mechanisms 504I-504L to retract back such that, when in a compressed state, the securing mechanisms 504I-504L may not lie outside a largest diameter of the tapered portion 512.

Figure 5B:
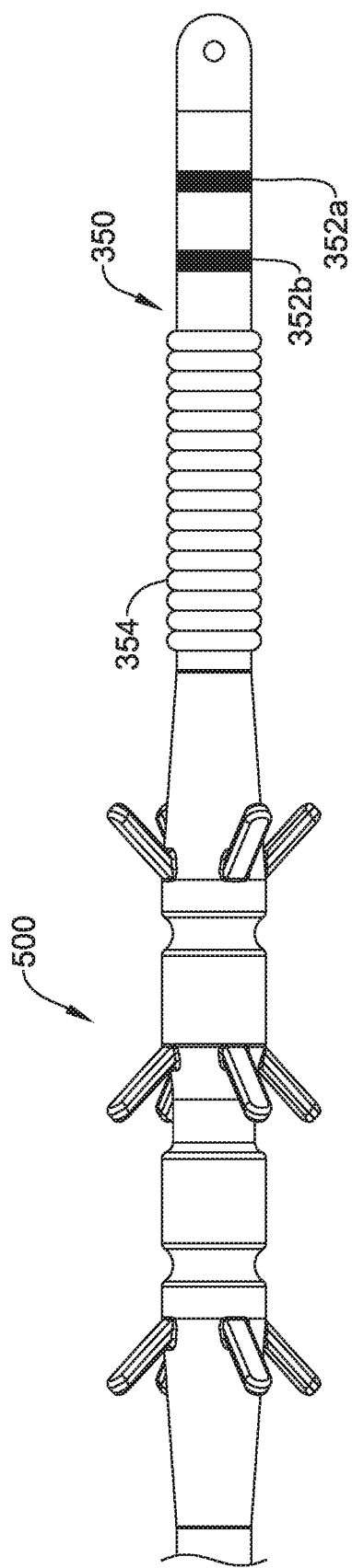
FIG. 5B shows the fifth exemplary retention device coupled to a lead.

FIG. 5B shows the retention device 500 coupled to the illustrative lead structure 350. The configuration and operation of the lead 350 with the retention device 500 may be similar to the lead 130 with the retention device 100 described in regard to FIG. 1B.

The described retention devices of FIGS. 1A, 2A, 3A, 4A, and 5A are by no means exhaustive. In some cases, the retention devices may include other configurations. Moreover, the examples depicted in FIGS. 1A, 2A, 3A, 4A, and 5A have been used to illustrate how the retention device may be customized to potentially optimize its performance and/or meet the requirements of the physician and patient. For example, in certain embodiments, the retention devices may be manufactured using 3D printing technology. In addition, in certain embodiments, the retention device may include six 60 A durometer reliance based silicone tine shaped securing mechanisms. In another embodiment, the retention device may include three soft 3D printed tine shaped securing mechanisms. In further embodiments, the retention device may include four nitinol talon shaped securing mechanisms. Other quantities of securing mechanisms and materials therefore may be used; in some examples, a retention device may include each of nitinol hooks and polymeric tines. As such, the final design may be configured based on a multiple of factors including, but no limited to, reliability, patient comfort, implantation locations and circumstances, etc.

FIGS. 6A-6F depict an illustrative three incision method for implanting a lead in a patient 600. Beginning with FIG. 6A, certain anatomy of the patient 600 is highlighted including a heart 602 and sternum 604. A xiphoid incision 606 may be made just to the left of and superior of the xiphoid near the lower portion of the sternum 604, and an axillary incision may be made near the left axilla of the patient 600, as shown at 608. An insertion tool 610 may be used in the procedure. The insertion tool 610 may have a handle 612 at a proximal end 618, and an elongate shaft 614 extends distally from the handle 612 toward a distal dissecting tip 620 that includes an attachment feature 616. The attachment feature 616 is shown as a suture opening, however, other suitable attachment features known in the art may be used. The distal tip 620 may be shaped for dissection of subcutaneous tissue. In one example, the distal tip 620 has a tapered blunt tip, allowing for passage by dissection through subcutaneous tissue without encouraging piercing through the epidermis. A channel(s) may be provided in the insertion tool 610 to allow infusion of fluids for antiseptic, anti-inflammatory, pain reduction, or other purposes at the dissecting tip or along the length thereof. If ingrowth or adhesion is desired, a tissue adhesive or steroid may be infused as well. As shown by the arrow in FIG. 6A, the insertion tool 610 may be inserted through the xiphoid incision 606 and advanced toward the axillary incision 608.

Figure 6A:
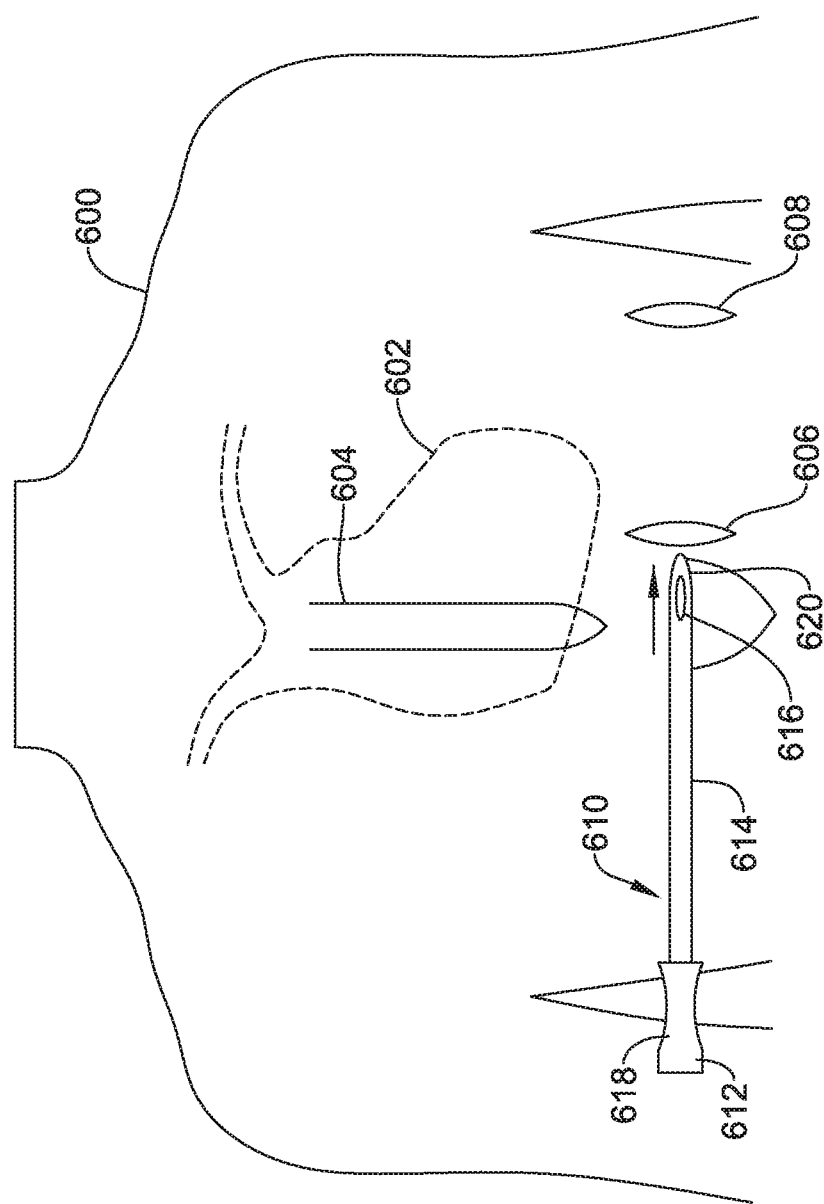
Figure 6B:
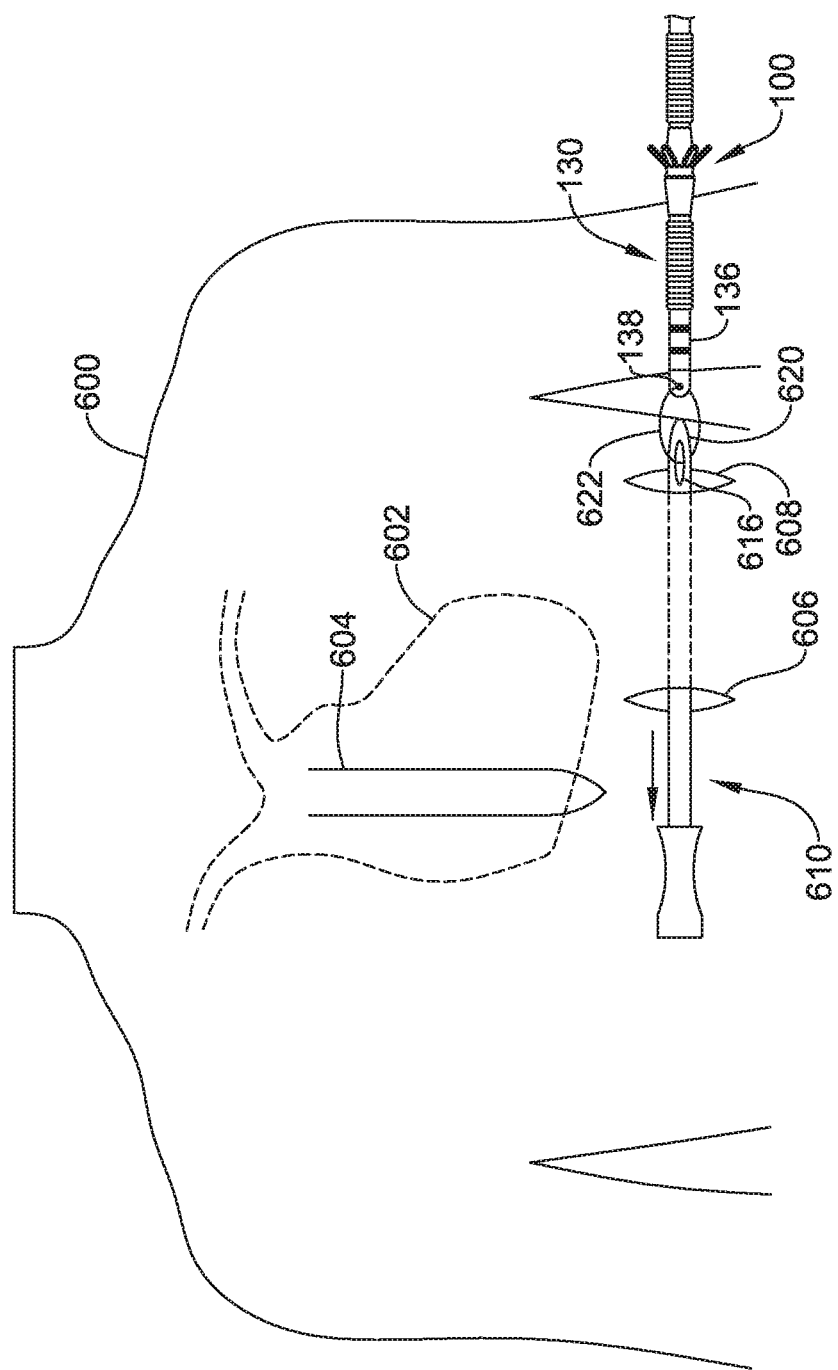

As shown in FIG. 6B, the lead 130 is prepared for use by applying the retention device 100 thereon at a desired location such as by sliding the retention device 100 over the proximal or distal end of the lead 130. The retention device 100 may be secured onto the lead 130 by tightening a suture thereon. Alternatively, the lead 130 may be provided by the manufacturer with the retention device 100 pre-attached and bonded to the lead 130, such as by using an adhesive, welding, heating, shrinking, or co-manufacturing process such as insert molding. The retention device 100 may include a longitudinal slit to allow lateral placement onto a lead, if desired. In some examples, a sheath may be placed over the lead 130 and retention device 100 to aid in holding the retention device 100 at the desired location on the lead, and to hold the securing mechanisms of the retention device in a compressed state, preventing them from engaging tissue during implantation prior to reaching a desired implant position.

Figure 6C:
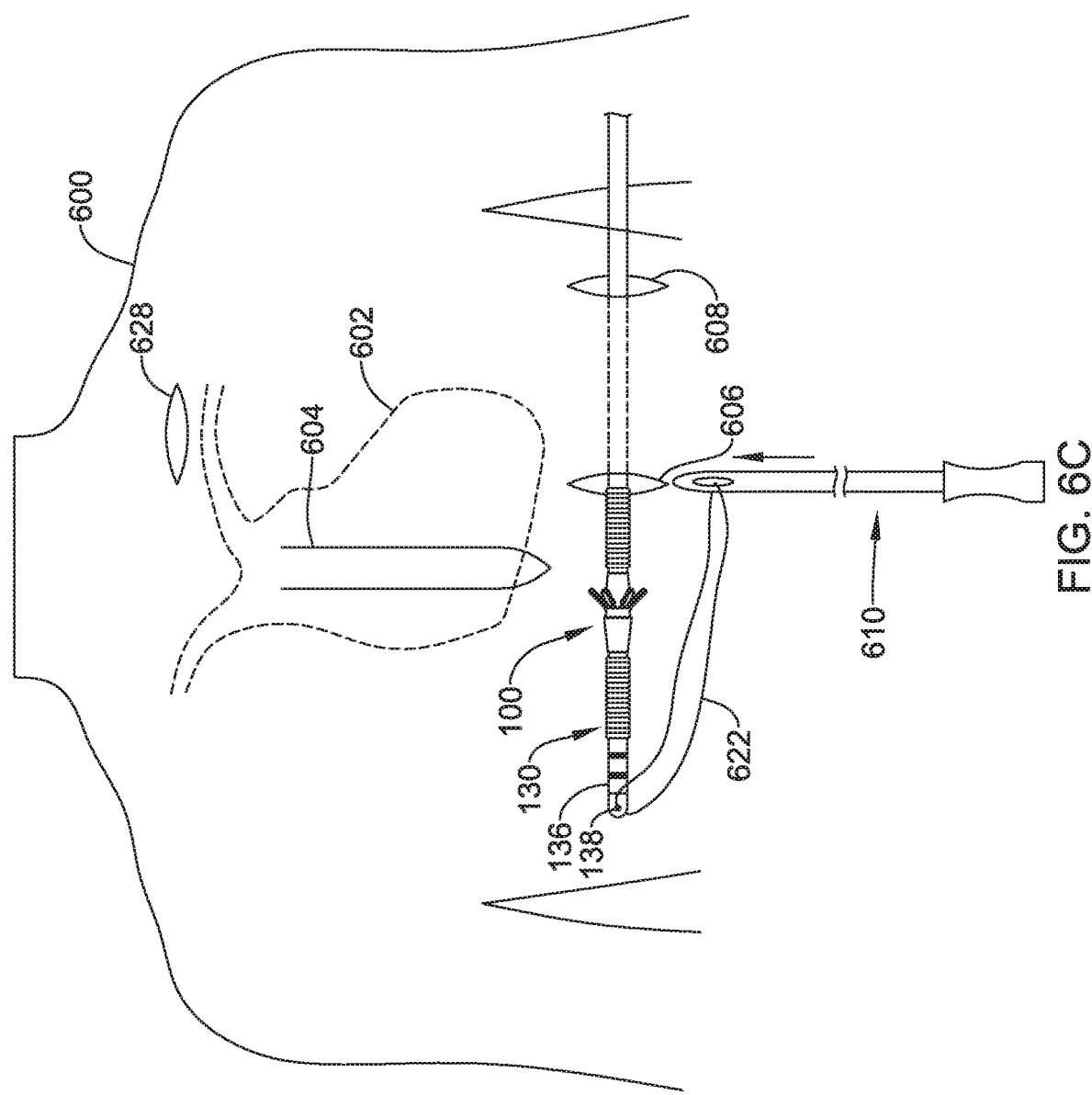

The insertion tool 610 may be inserted into the xiphoid incision until its distal tip 620, including the attachment feature 616, can be accessed through the axillary incision 608. Then a suture 622 may be used to attach the attachment feature 616 of the insertion tool 610 to an attachment feature 138 on the distal tip portion 136 of the lead 130. Next, the insertion tool 610 may be withdrawn through the xiphoid incision 606, with the suture 622 pulling the lead 130 into the patient's 600 subcutaneous tissue through the axillary incision 608. The end of this pulling step is shown in FIG. 6C, where the attachment feature 138 at the distal tip portion 136 of the lead 130 extends through the xiphoid incision 606. At the end of this step, a proximal plug 626 of the lead 130 may be located relatively near the axillary incision 608, though this may depend on the anatomy of the patient 600 and the length of the lead 130.

In the example shown in FIG. 6C, the suture 622 remains attached to the insertion tool 610, which is shown in alignment with the sternum 604 in preparation for the next step of the procedure. An upper incision 628 may be made a short distance to the left of the sternum 604 at a location that is superior to the xiphoid incision 606, approximately along the left sternal margin. For example, the upper incision 628 may be located approximately 8 to 18 cm superior of the xiphoid incision 606, and 1-3 cm left of the sternum 604. The upper incision 628 may also be described as level with or inferior to the manubrium and/or level with or superior to the atria of the heart. These particular locations are illustrative and not required; various implant locations can be used. The insertion tool 610 may then be reinserted into the xiphoid incision and advanced generally parallel to the sternum 604 toward and through the upper incision 628.

Figure 6D:
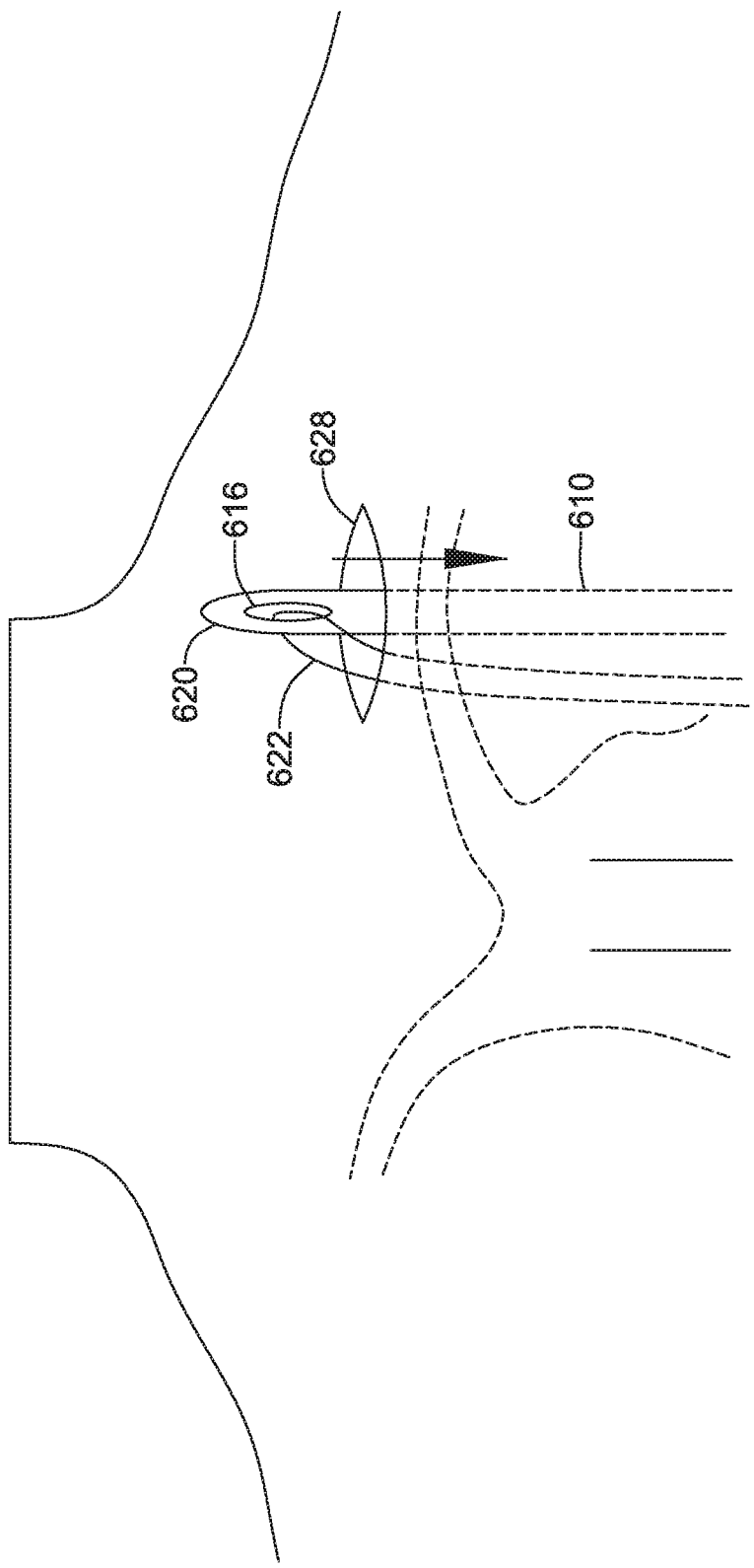
Figure 6F:
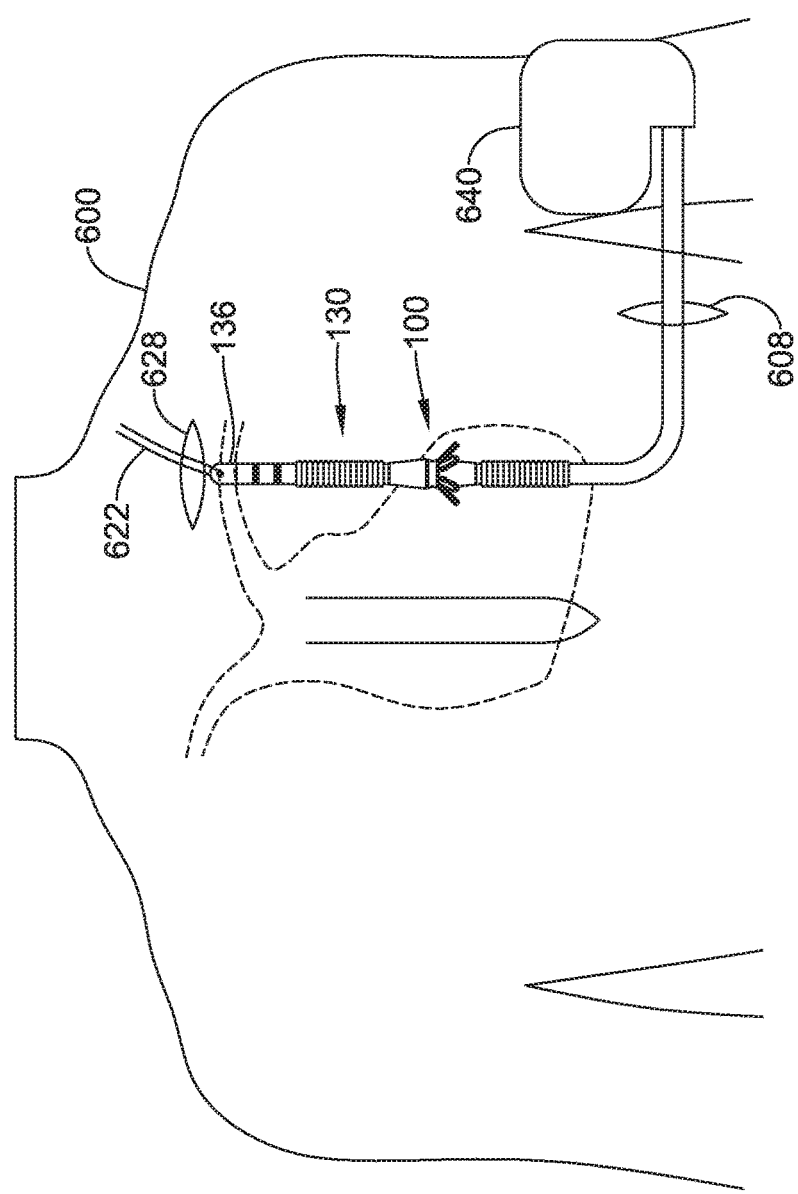

Turning to FIG. 6D, the distal tip 620 of the insertion tool 610 extends out of the upper incision 628 until the attachment feature 616 can be accessed. Next, a forceps (not shown) may be used to grasp the suture 622, which may be cut from the attachment feature 616. The insertion tool 610 may then be withdrawn. Turning to FIG. 6E, the forceps (not shown) may be used to pull the suture 622 through the upper incision 628, drawing the lead 130 through the xiphoid incision 606 into the patient 600 and through the tunnel formed by the insertion tool 610. The suture 622 may be pulled until the lead 130 achieves the position shown in FIG. 6F, where the distal tip portion 136 of the lead 130 and its attachment feature 138 may be accessed at the upper incision 628 and the proximal plug 626 of the lead 130 may be attached to a canister 640. The canister 640 may then be implanted through the axillary incision 608 and sutured to the patient 600 tissue. In addition, in some cases, an introducer sheath (not shown) may be used to compress the securing mechanisms 104A-104D into a pre-deployed state. When the lead 130 has reached the position shown in FIG. 6F (i.e., the deployment position), the sheath may be removed or withdrawn and the securing mechanism 104A-104D may expand or extend into its deployed state to engage, push against, and/or anchor the lead 130 to the patient 600 tissue (e.g. the tunnel formed by the insertion tool 610).

Once emplaced, the sheath over the retention device 100 (not shown) is removed and the securing mechanisms of the retention device 100 expand from their compressed state to engage patient tissue. This may provide several potential benefits. For instance, the retention device 100 may improve stability during implantation of the lead 130. The retention device 100 may also improve stability during acute implant duration, prior to tissue ingrowth. In some cases, the retention device 100 may potentially improve long term stability, including a chance for less noise due to electrode movement and reduced inappropriate shocking. In some cases, the retention device 100 may eliminate the need for suturing the lead down to the patient fascia. That is, a physician may implant the device without suturing the retention device 100 to the patient, instead relying on the securing mechanisms thereof to hold it in place.

Several modifications may be made to the method of implanting the subcutaneous defibrillator described in FIGS. 6A-6F. For example, several alternative structures for leads and retention devices may be used and additional steps/features may be are provided. In some examples, the retention device may take the form of the retention devices 200, 300, 400, or 500 shown in FIGS. 2A-2B, 3A-3B, 4A-4B, and 5A-5B. In some examples, rather than the steps of FIGS. 6E-6F to place the lead 130 over the ribs and alongside the sternum, a substernal approach may be taken by advancing the lead beneath the ribs, such as described in US PG Patent Publication Nos. 20140330248, 20140330327, and/or 20170021159, the disclosures of which are incorporated herein by reference. In other examples, access may be had to the internal thoracic vein at an intercostal location or through the superior epigastric vein and/or the musculophrenic vein, as taught in US PG Patent Publication No. 20180036527, titled IMPLANTATION OF AN ACTIVE MEDICAL DEVICE USING THE INTERNAL THORACIC VASCULATURE, the disclosure of which is incorporated herein by reference.

Figure 7A:
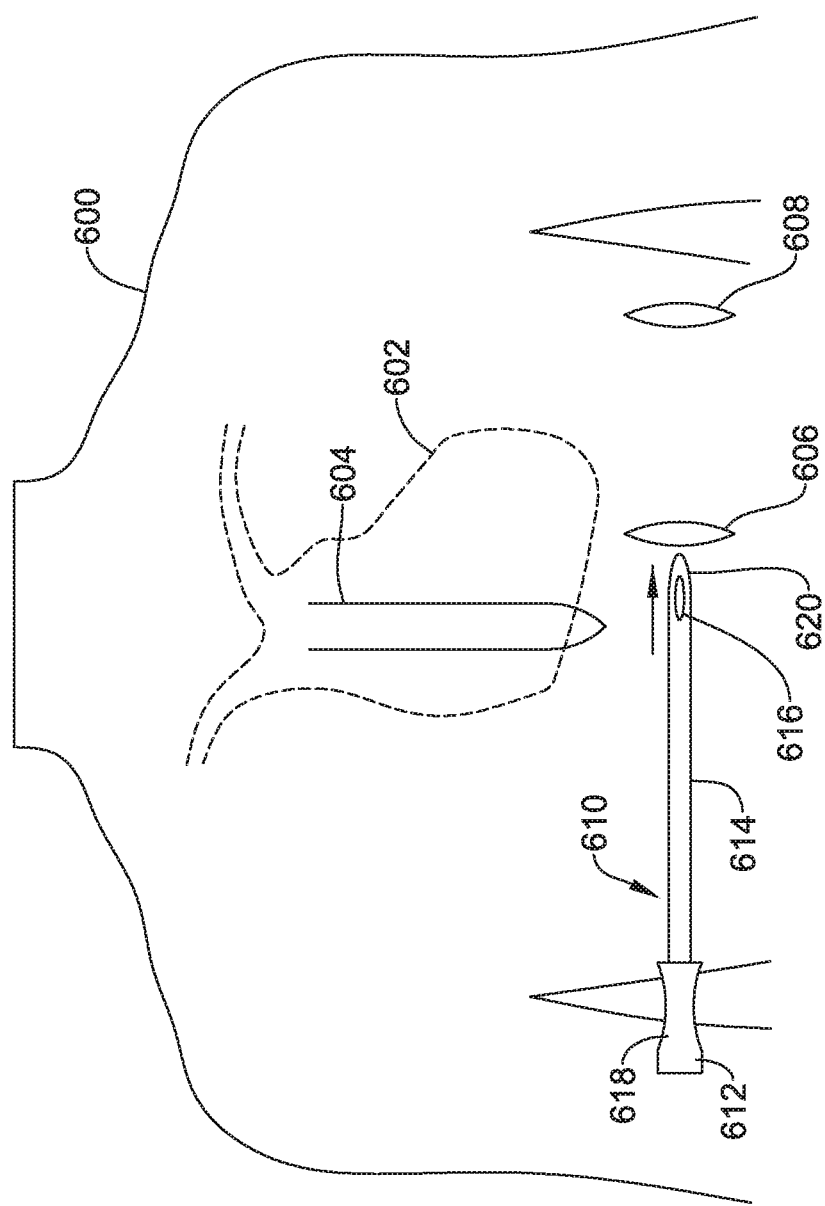

FIGS. 7A-7E depict an illustrative two incision method of implanting a lead in a patient 600. The beginning of the two incision method may be similar to the three incision method depicted in FIGS. 6A-6B. As shown in FIG. 7A, the xiphoid incision 606 and the axillary incision 608 are made. The insertion tool 610 may then be inserted through the xiphoid incision 606 and advanced toward the axillary incision 608.

Figure 7B:
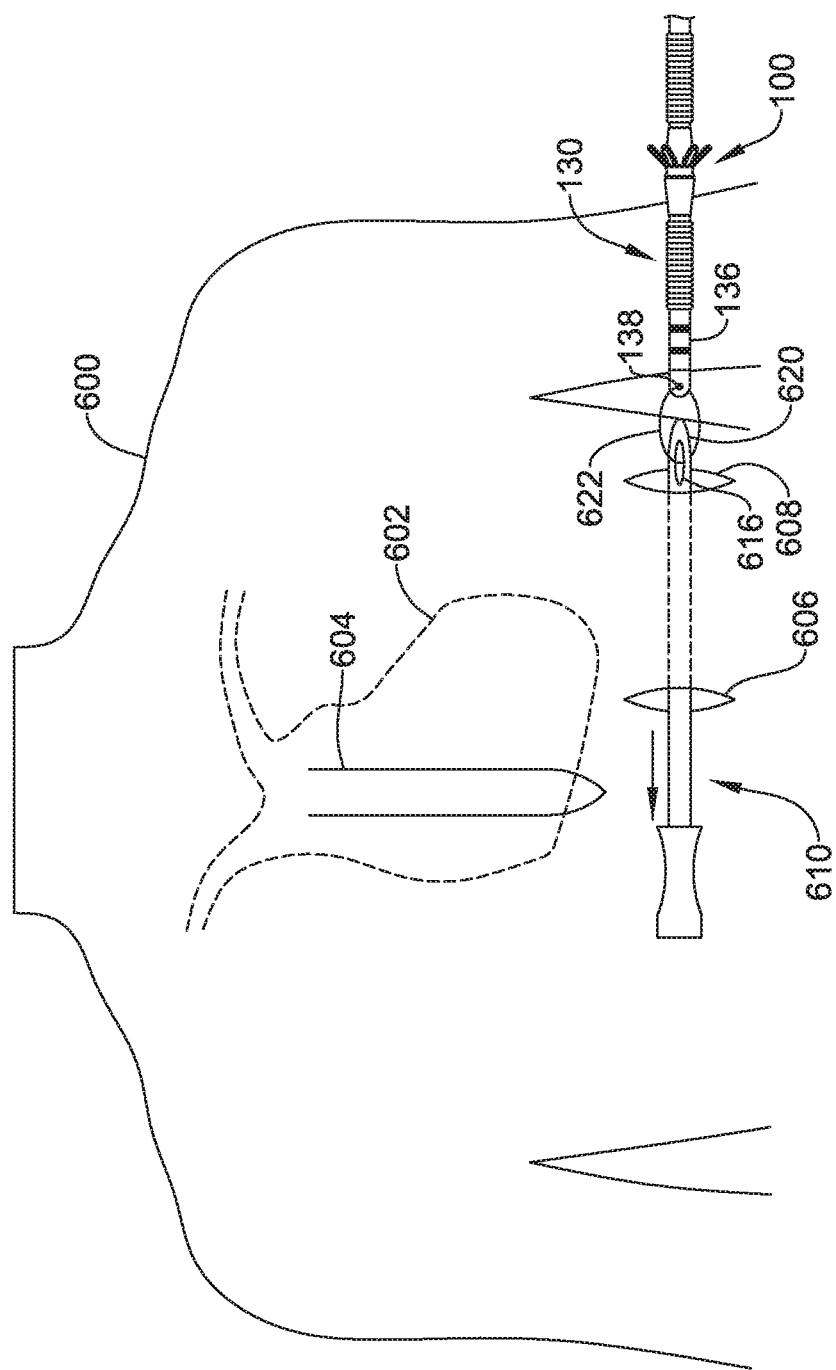

As shown in FIG. 7B, the insertion tool 610 may be inserted into the xiphoid incision 606 until its distal tip 620, including the attachment feature 616, can be accessed through the axillary incision 608. Then the suture 622 may be used to attach the attachment feature 616 of the insertion tool 610 to the attachment feature 138 on the distal tip portion 136 of the lead 130. If needed, the lead 130 may be prepared by attaching a retention device 100 (before or after attachment to the insertion tool 610). Alternatively, the retention device 100 may be permanently attached to the lead 130 during manufacturing thereof.

In some examples, a sheath may be placed on the lead, either at the time of surgery or as a preloaded system, to prevent the retention device 100 engaging tissue during its introduction into the patient. Next, the insertion tool 610 may be withdrawn through the xiphoid incision 606, with the suture 622 pulling the lead 130 into the patient's 600 subcutaneous tissue through the axillary incision 608. Alternatively, a sheath may be used to advance the lead 130 into tissue without the use of the suture to pull the lead 130. The end of this pulling step is shown in FIG. 7C, where the attachment feature 138 at the distal tip portion 136 of the lead 130 extends through the xiphoid incision 606 and forceps (not shown) may be used to grasp the suture 622, which may be cut from the attachment feature 616. At the end of this step, the proximal plug 626 of the lead 130 may be located relatively near the axillary incision 608, though this may depend on the anatomy of the patient 600 and the length of the lead 130.

If used, a sheath may be removed after the lead has been pulled to and through the axillary incision. Alternatively, the sheath may be kept in place until implantation is complete. In still other alternatives, no sheath is used during this tunneling and pulling step. For example, no sheath may be needed during pulling from the axillary incision to the xiphoid incision if the securing mechanisms are biased to allow passage through tissue in one direction but not the other.

Figure 7D:
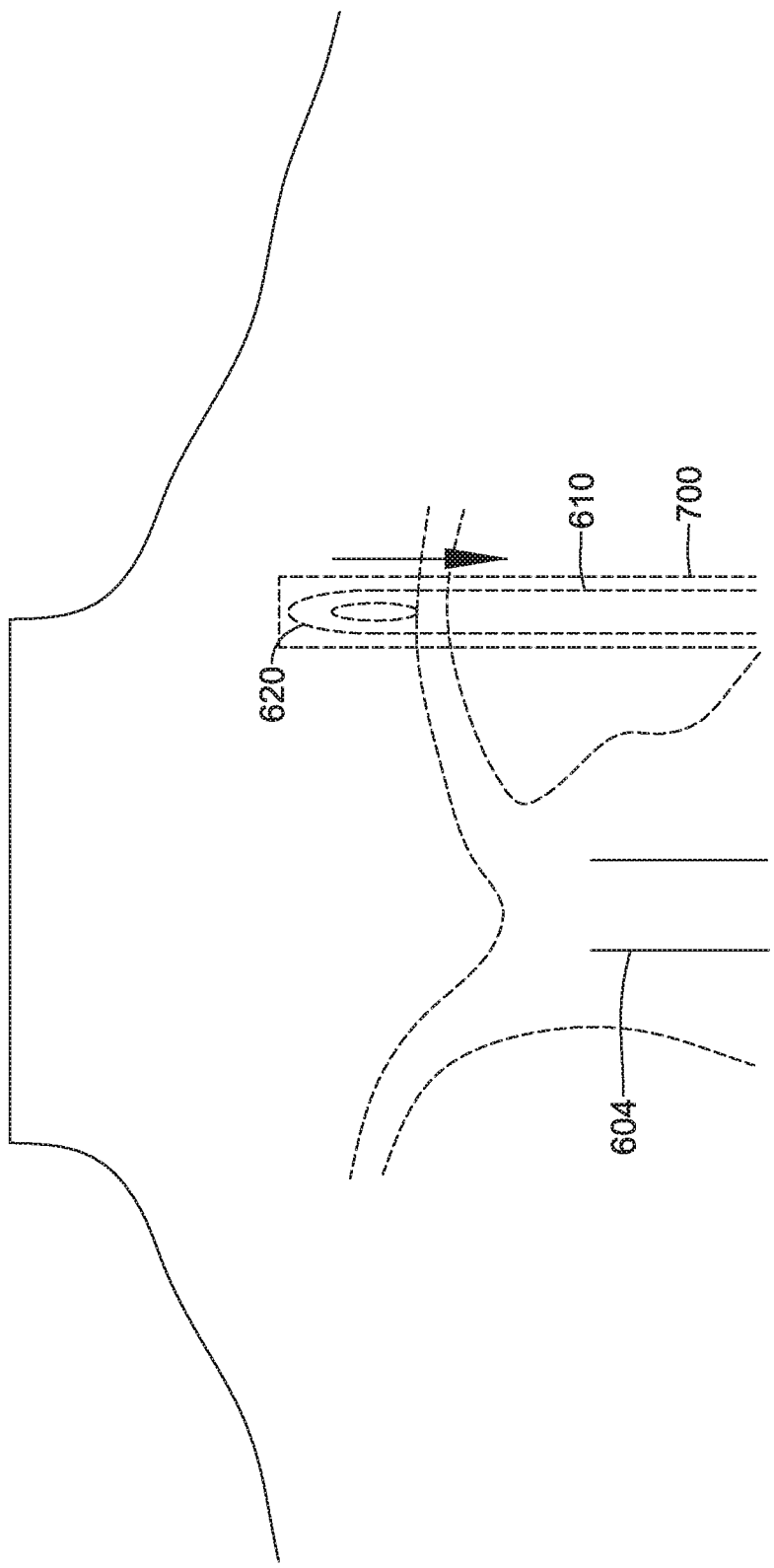

In the example shown in FIG. 7C and as described herein, the distal tip 620 of the insertion tool 610 may be shaped to allow for passage by dissection through subcutaneous tissue. Accordingly, the insertion tool 610 may be reinserted into the xiphoid incision 606 and advanced generally parallel to the sternum 604 to create a tunnel 700, as shown in FIG. 7D. Thought not shown, an introducer sheath may be placed over the insertion tool 610 during the step shown in FIGS. 7C-7D. The insertion tool 610 may then be withdrawn, with the introducer sheath left in place.

Figure 7E:
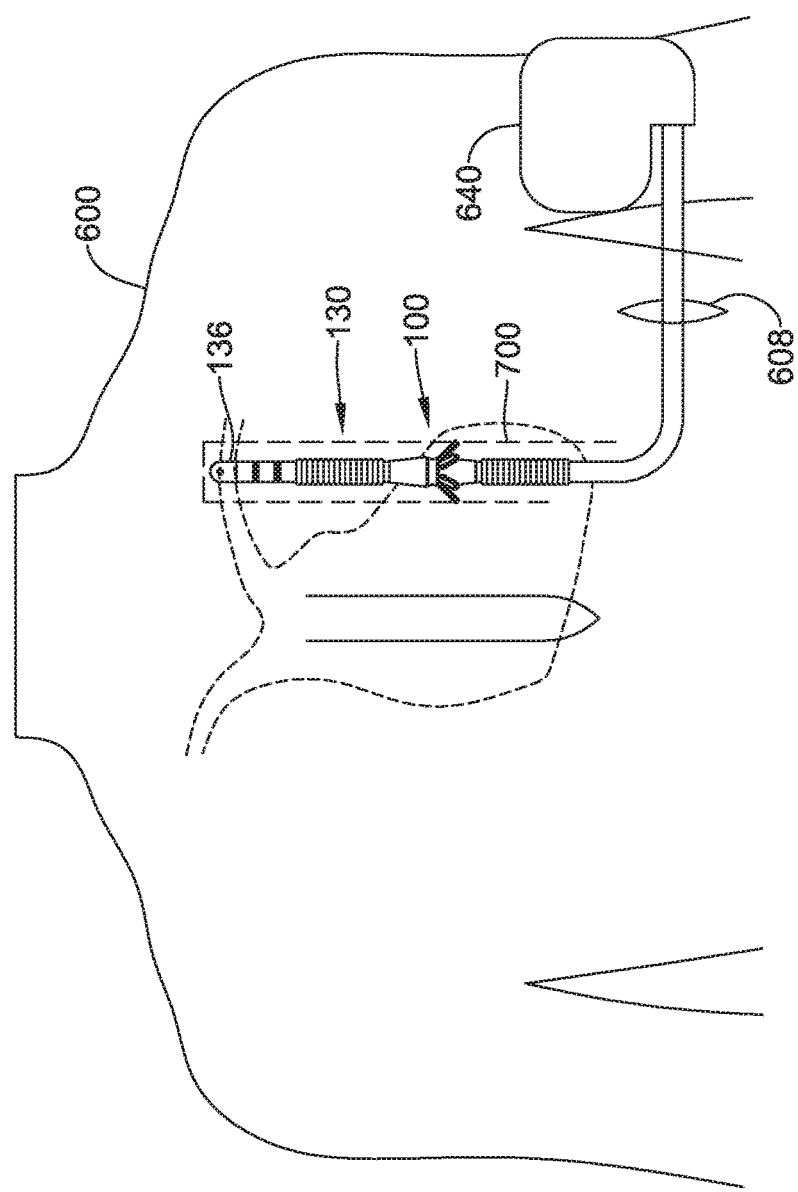

As shown in FIG. 7E, the lead 130 may be reinserted into the xiphoid incision 606 and advanced generally through the tunnel 700 and retained introducer sheath. The introducer sheath is then split and removed over the lead. If the introducer sheath is used in both passage through the axillary-xiphoid tunnel and in the parasternal tunnel, it would be removed at the left axilla. If the introducer sheath is used only in the parasternal tunnel, or is removed after the passage from axilla to xiphoid and a second introducer sheath used for the parasternal tunnel, then the introducer sheath would be removed at the xiphoid. The proximal plug 626 of the lead 130 may then be attached to the canister 640 and the canister 640 may be implanted through the axillary incision 608 and sutured to the patient 600 tissue. The two incision technique shown in FIGS. 7A-7E may be generally similar, except with respect to the use of the retention device, to certain examples in U.S. Pat. No. 7,655,014, titled APPARATUS AND METHOD FOR SUBCUTANEOUS ELECTRODE INSERTION, the disclosure of which is incorporated herein by reference.

Figure 8A:
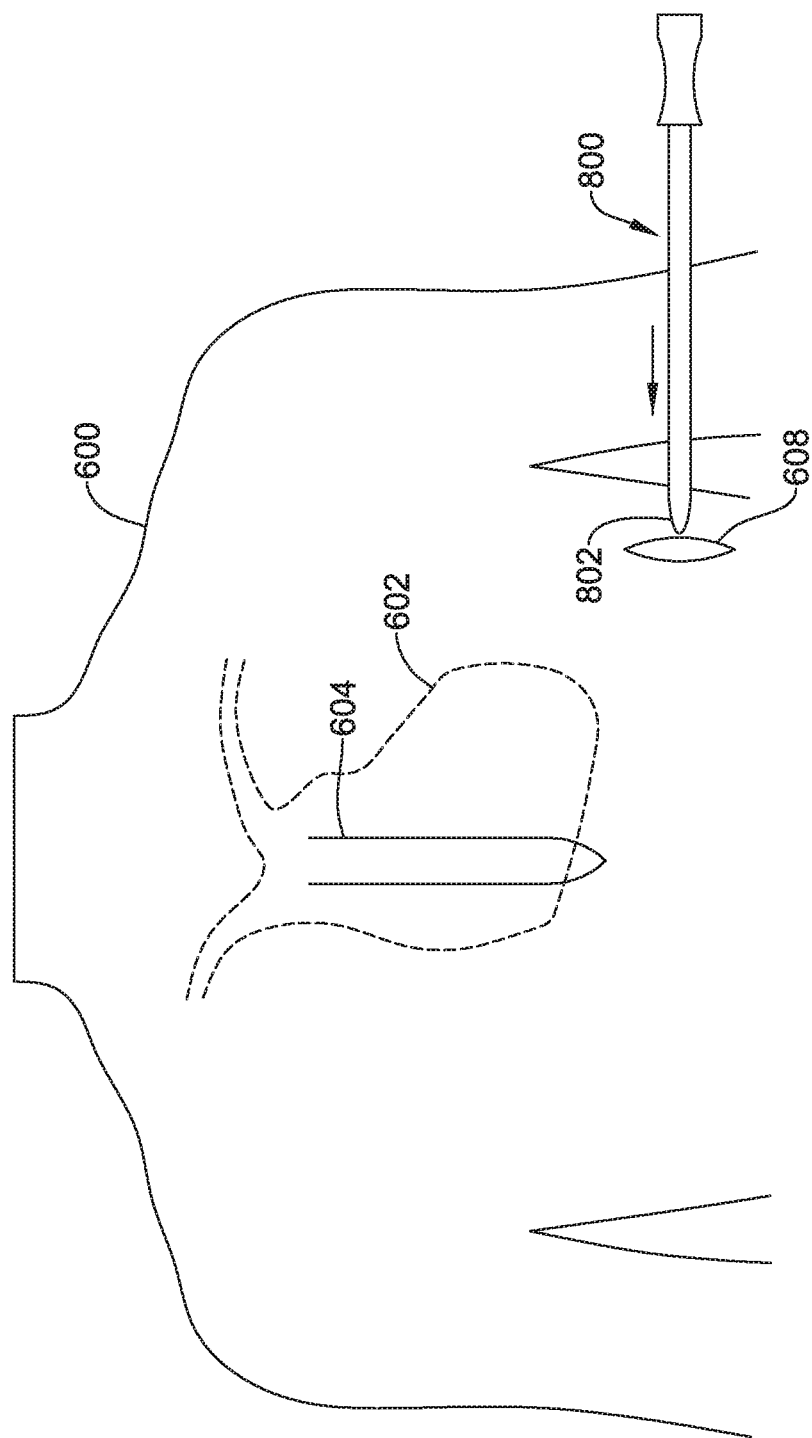
Figure 8C:
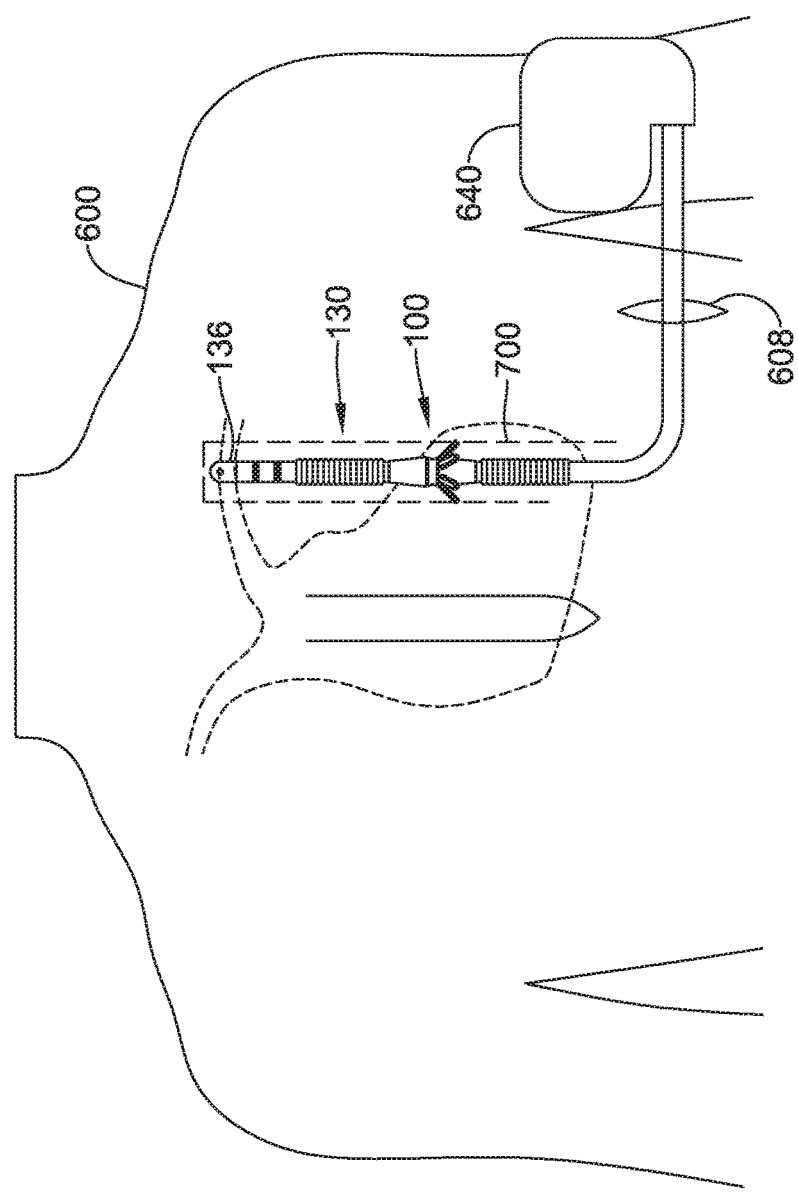

FIGS. 8A-8C depict an illustrative one incision method of implanting the S-ICD in the patient 800. As shown in FIG. 8A, the axillary incision 608 is made and an insertion tool 800 may be inserted through the axillary incision 608. The insertion tool 800 may be similar to the insertion tool 610 (from FIGS. 6A-6D and 7A-7D) in that the insertion tool 800 may also have a distal tip 802 that is shaped to allow for passage by dissection through subcutaneous tissue. In addition, the insertion tool 800 may be deflectable or steerable and may be used to create a tunnel 804 from the axillary incision 608, just to the left of and superior of the xiphoid near the lower portion of the sternum 604, and advanced generally parallel to the sternum 604, as shown in FIG. 8B. In an example, the insertion tool 800 is advanced as shown with an introducer sheath thereon. The insertion tool 800 may then be withdrawn, keeping the introducer sheath in place As shown in FIG. 8C, the lead 130 may be positioned at a desired location in the tunnel 804 by insertion through the introducer sheath 802. Removal of the introducer sheath then allows the retention device to become engaged to the patient tissue at a desired location as the securing mechanisms on the retention device expand from a compressed state to an uncompressed state. The proximal plug 626 of the lead 130 may then be attached to the canister 640 and the canister 640 may be implanted through the axillary incision 608 and sutured to the patient 600 tissue.

In the various examples, shown, the end location for the retention device 100 may be in several different spots. In some examples, the retention device 100 will be placed at the distal end of the lead and will engage tissue more or less near the sternum superior to one or more electrodes of the lead 130. In other examples, the retention device 100 will end up near the xiphoid process, inferior to the anatomical position of the electrodes on the lead 130. In other examples, the retention device 100 may be positioned along the inframammary crease.

As shown above, three general implantation methods are shown. Various alternatives to steps and devices shown are identified. At a high level, a three incision technique is shown with a sternal incision, a xiphoid incision, and an axillary incision, wherein one or two sheaths may be used to pass a lead having an anchoring device thereon through one or more of the axilla-xiphoid tunnel or the parasternal tunnel, wherein the sheath may be provided to perform one or more of supporting the lead passage, maintaining a tunnel for lead insertion, and/or to restrain or retain securing mechanisms on the lead. In the three incision technique, the present invention provides options that reduce the suturing at the xiphoid incision and/or which increase the anchoring strength at the xiphoid incision.

At a high level, a two incision technique is shown that omits the sternal incision of the three incision technique; a sheath is used to secure the parasternal tunnel and may additionally serve to support lead passage and/or to restrain or retain securing mechanisms on the lead. In the two incision technique, the present invention again provides options that may reduce the suturing at the xiphoid incision and/or which increase the anchoring strength at the xiphoid incision.

At a high level, a single incision method may omit each of the xiphoid and sternal incisions; a sheath is used to secure the parasternal tunnel and may additionally serve to support lead passage and/or to restrain or retain securing mechanisms on the lead. The present invention, for the single incision method, better facilitates omission of at least the xiphoid incision by providing anchoring mechanisms at an appropriate spot on the lead for this purpose. The single incision method may use a curved, telescoping and/or deflecting/steerable tunneling system, such as shown in US PG Pat. Pub. No. 20170020551, titled MINIMALLY INVASIVE METHOD TO IMPLANT A SUBCUTANEOUS ELECTRODE, the disclosure of which is incorporated herein by reference. A single incision method may also or instead use a method as shown in U.S. Provisional Patent Application No. 62/546,832, titled SINGLE INCISION SUBCUTANEOUS IMPLANTABLE DEFIBRILLATION SYSTEM, the disclosure of which is incorporated herein by reference.

As illustrated in these examples, the present invention facilitates flexibility in selection of the implant procedure. For example, with a very active or young patient where lead migration is a great concern, or for a patient with a lot of adipose tissue that may make lead anchoring more challenging, a multiple incision technique may be performed using both suturing techniques and the retention device to hold the lead in place by multiple approaches. For other patients, a single incision technique may be used relying solely on the retention device, or a two incision technique that omits a xiphoid incision relying on an intermediate fixation point as well as, optionally, distal tip fixation. The physician has the option of distal tip fixation, and intermediate suture-based fixation in addition to relying on the retention device 100. Such flexibility may allow the physician to make changes to the planned procedure intraoperatively, without having to discard a lead that is deemed unsuitable to the particular patient. A physician may determine, through gentle tugging at the proximal (or distal) end of the lead, whether sutures need to be applied.

Figure 9:
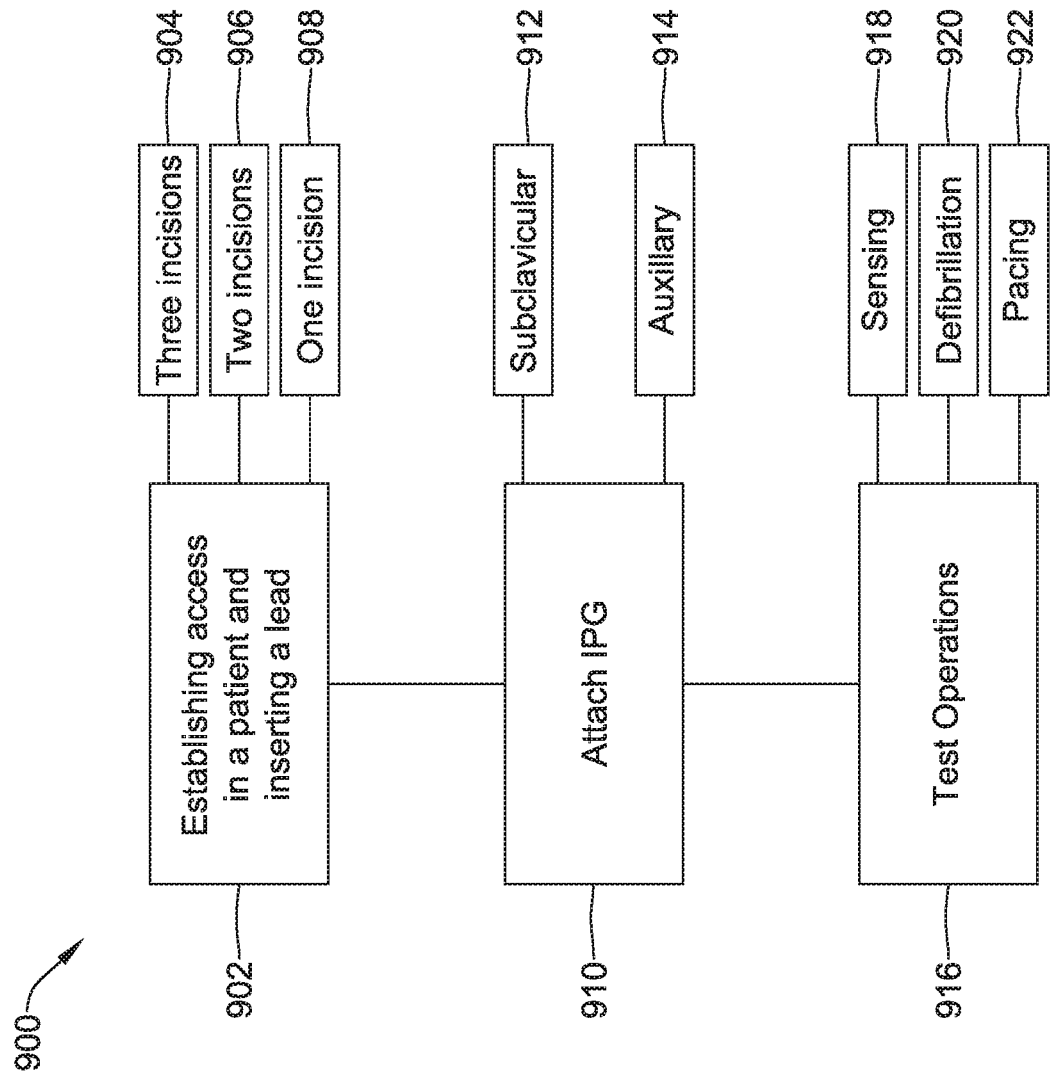
FIG. 9 is a block flow diagram for an illustrative method.

FIG. 9 is a block flow diagram of an illustrative method 900 for providing a cardiac stimulus system to a patient. As shown, the method 900 comprises establishing access in a patient and inserting a lead 902, attaching an implantable pulse generator (IPG) to the lead 910, and performing test operations 916. The IPG may also be referred to herein as a canister or implantable canister.

For example, establishing access to the patient and inserting a lead 902 may include using a three incision implantation method 904, such as described above relative to FIGS. 6A-6F. In another example, establishing access to the patient and inserting a lead 902 may include using a two incision implantation method 906, generally as shown above relative to FIGS. 7A-7E. In another example, establishing access to the patient and inserting a lead 902 may include using a one incision implantation method 908, generally as shown above relative to FIGS. 8A-8C.

Regardless of the incision method used, once the lead is at a selected position or configuration in the patient, a securing mechanism located on a retention device of the lead may engage, push against, and/or anchor the lead to the patient tissue. Suturing to the fascia may thus be reduced or omitted.

In an example, attaching an IPG to the lead 910 may include attaching to a canister located in a subclavicular location 912, historically a common place to put an implanted canister for a transvenous defibrillator or pacemaker. In another example, attaching to an IPG may include attaching to a canister located in an axillary position 914, such as that used with the S-ICD System. Other IPG locations may be used. Attachment may be directly to the IPG or to a splitter, yoke, or lead extension, if desired.

In an example, test operations 916 may be used to verify one or both of device functionality and efficacy. For example, sensing operations 918 may be tested and configured to check for adequate signal availability, for example, or by setting gain, filtering, or sensing vector selection parameters. Defibrillation operations 920 may be tested by inducting an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing 920 may include determining for a given patient an appropriate defibrillation threshold, and setting a parameter for therapy delivery at some safety margin above the defibrillation threshold.

In an example, pacing testing operation 922 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

As noted above, the illustrative retention devices may be formed of any biocompatible material. Some examples include elastic, biocompatible alloys capable of forming stress induced martensite (SIM). Nitinol (TiNi) is an example of such materials. A retention device may be formed from stainless steel, such as high tensile stainless steel, or other materials, including metals and metal alloys, such as tungsten, gold, titanium, silver, copper, platinum, palladium, iridium, ELGILOY nickel-cobalt alloys, cobalt chrome alloys, molybdenum tungsten alloys, tantalum alloys, titanium alloys, etc. A retention device may be formed from a lubricious polymer, such as a fluorocarbon (e.g., polytetrafluoroethylene (PTFE)), a polyamide (e.g., nylon), a polyolefin, a polyimide, or the like). A retention device may be formed of polyethylene, polyvinyl chloride (PVC), ethyl vinyl acetate (EVA), polyethylene terephthalate (PET), and their mixtures and copolymers. Another useful class of polymers is thermoplastic elastomers, including those containing polyesters as components. A retention device may also be comprised of such materials as soft thermoplastic material, polyurethanes, silicone rubbers, nylons, polyethylenes, fluorinated hydrocarbon polymers, and the like. A retention device may also be of a member selected from a more flexible material such as low density polyethylene (LDPE), polyvinylchloride, THV, etc. Still in further embodiments, a retention device may be composed of a combination of several these materials. In certain embodiments, a retention device may be formed of, impregnated with, or comprise a maker made of a radiopaque material such as, for example and without limitation barium sulfate (BaSO4), bismuth trioxide (Bi2O3), bismuth subcarbonate (Bi2O2CO3), bismuth oxychloride (BiOCl), and tungsten.

Retention devices may be formed by molding, such as injection molding, or insert molding. In some examples, different parts or layers may be included such as by, for example, extruding a core tube having one or a plurality of layers (such as a lubricious inner layer with a tie layer thereon to allow ready attachment of additional material) of the retention device and insert molding an outer surface thereon of a different material, with the securing mechanisms added via the insert molding process. In another example, a wire member may be used as a starting point for an insert molding process, wherein the wire member comprises a set of tines to use as securing mechanisms on which a polymeric material is added.

Lead structures for use with the present invention may take any suitable type and use any suitable material, such as the materials noted above. Internal longitudinal or lateral support members, such as braids, core wires, etc. may be provided. Extrusion or molding may be used for lead manufacture. Internal conductors in the lead may be formed of any suitable material (stainless steel, titanium, gold, silver, or any other conductive material may be used) and may take any suitable form, such as simple wires, coated wires, braided or wound wires, drawn wires, and/or drawn filled tubes, or other structures. The lead may include on all or a portion thereof various coatings such as an anti-microbial coating to reduce the likelihood, severity, and/or progression of infection.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems.

The present invention may be used for non-cardiac devices such as, for example and without limitation, the Precision Novi, and/or Precision Spectra implantable neuromodulation devices offered by Boston Scientific. Any suitable lead structure may be used, such as leads adapted for subcutaneous implantation for cardiac monitoring or therapy purposes, and/or leads adapted for use in spinal, deep brain, or peripheral neuromodulation systems such as vagus or sacral nerve therapies. When used in a neuromodulation system, the methods of FIG. 9 may be modified to swap out the test operations at 916 to determining appropriate therapy settings including electrode selection/positioning and threshold testing to identify suitable waveforms, frequencies, pulse widths, and current or voltage levels, such as paresthesia mapping and other therapy effects mapping, as are well known in the neuromodulation field.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with The claimed invention is:

1. A method of implanting an implantable lead in a patient comprising the use of:
   an implantable lead having a first end for coupling to an implantable medical device and a second end for implantation at a target site in a patient, with a lead body extending therebetween; and
   a retention device comprising an elongate body having an outer surface and defining a bore extending therethrough, and one or more securing mechanisms each having a first end coupled to the outer surface of the elongate body and a second end configured to push against tissue of the patient, wherein the one or more securing mechanisms are configured for each of a compressed, pre-deployed state and a deployed state;
   wherein an entirety of each securing mechanism overlies a cylindrical portion of the elongate body when the retention device is in both the compressed and deployed states;
   wherein the outer surface of the elongate body has a receiving region of lesser diameter than another region of the outer surface of the elongate body such the when the securing mechanism is in the compressed, pre-deployed state, the receiving region allows the securing mechanism to be compressed therein such that the securing mechanism does not lie outside a largest diameter of the outer surface;
   wherein the method comprises:
   placing a portion of the implantable lead through the bore of the retention device and tying a suture around the retention device thereby reducing a diameter of the bore and securing the retention device onto the implantable lead;
   inserting the implantable lead into a patient with the retention device placed on the lead at the desired location thereon and with a sheath compressing the securing mechanism of the retention device in the compressed, pre-deployed state; and
   at least partly withdrawing the sheath such that the one or more securing mechanisms expand to the deployed state to anchor the implantable lead to tissue of the patient.

2. The method of claim 1 wherein the step of inserting the implantable lead is performed by making a single incision, advancing an insertion tool having the sheath thereon through the incision and to a selected position in the patient, removing the insertion tool while keeping the sheath in place, and then inserting the implantable lead into the sheath such that the sheath compresses the securing mechanism of the retention device in the compressed, pre-deployed state.

3. The method of claim 1 wherein the step of inserting the implantable lead is performed by:
   making a first incision and a second incision;
   making a first tunnel between the first and second incisions;
   making a second tunnel from the second incision to an end location;
   passing at least a portion of the lead with the retention device thereon through the first tunnel with the sheath thereover or through the sheath; and
   passing at least the second end of the lead through the second incision to the end location.

4. The method of claim 3 wherein the outer surface of the retention device includes a recess configured to receive a suture to secure the retention device in a desired location on the lead, and the step of inserting the implantable lead is performed such that the retention device is accessible near the second incision, and the method further comprises using a suture to anchor the retention device to the patient using the recess to receive the suture at or near the second incision such that the securing mechanisms and the suture are both used to secure the lead in the selected position.

5. The method of claim 1 wherein the step of inserting the implantable lead is performed by:
   making a first incision, a second incision and a third incision;
   making a first tunnel between the first and second incisions;
   making a second tunnel between the second and third incisions;
   passing at least a portion of the lead with the retention device thereon through the first tunnel with the sheath thereover, or through the sheath; and
   passing at least the second end of the lead through the second incision to the third incision.

6. The method of claim 5 wherein the outer surface of the retention device includes a recess configured to receive a suture to secure the retention device in a desired location on the lead, and the step of inserting the implantable lead is performed such that the retention device is accessible near the second incision, and the method further comprises using a suture to anchor the retention device to the patient using the recess to receive the suture at or near the second incision such that the securing mechanisms and the suture are both used to secure the lead in the selected position.

7. A retention device for use with an implantable medical device (IMD) comprising:
   an elongate body including an outer surface, the elongate body defining a bore extending therethrough, the bore having a diameter sized to receive a portion of an implantable lead; and
   one or more securing mechanisms each having a first end coupled to the elongate body and a second end configured to push against tissue of the patient;
   wherein an entirety of each securing mechanism overlies a cylindrical portion of the elongate body;
   wherein the one or more securing mechanisms are configured to move from a pre-deployed compressed state to an expanded deployed state;
   wherein the outer surface of the elongate body includes a recess configured to receive a suture to secure the retention device on the lead, the lead configured such that tightening the suture while a lead is disposed within the bore reduces the diameter of the bore to secure the elongate body onto the lead; and
   wherein the outer surface of the elongate body has a receiving region of lesser diameter than another region of the outer surface of the elongate body such the when the securing mechanism is in the pre-deployed compressed state, the receiving region allows the securing mechanism to be compressed therein such that the securing mechanism does not lie outside a largest diameter of the outer surface.

8. The retention device of claim 7 wherein the one or more securing mechanisms comprise a plurality of securing mechanisms radially spaced from one another.

9. The retention device of claim 7, wherein the one or more securing mechanisms are made of a flexible material.

10. The retention device of claim 7, wherein the one or more securing mechanisms includes a first securing mechanism and a second securing mechanism and the first securing mechanism extends out from the elongate body at a first angle, and the second securing mechanism extends out from the elongate body at a second angle, wherein the first and second angles are equal.

11. The retention device of claim 7, wherein the one or more securing mechanisms further includes a first set of securing mechanisms and a second set of securing mechanisms, the second set of securing mechanisms spaced longitudinally away from the first set of securing mechanisms.

12. The retention device of claim 11, wherein the first set of securing mechanisms extends outward from the elongate body in a first direction at a first angle, and the second set of securing mechanisms extends outward from the elongated body in the first direction at a second angle, wherein the first and second angles are equal.

13. The retention device of claim 11, wherein the first set of securing mechanisms extends outward from the elongate body in a first direction at a first angle, and the second set of securing mechanisms extends outward from the elongated body in a second direction at a second angle, wherein the first and second angles are equal and the first and second directions are opposite one another such that the second ends of the first set of securing mechanisms are closer to the second ends of the second set of securing mechanisms than to the first ends of the second set of securing mechanisms.

14. The retention device of claim 11, wherein the first set of securing mechanisms extends outward from the elongate body in a first direction at a first angle, and the second set of securing mechanisms extends outward from the elongated body in a second direction at a second angle, wherein the first and second angles are equal and the first and second directions are opposite one another, and wherein the first ends of the first set of securing mechanisms are closer to the first ends of the second set of securing mechanisms than to the second ends of the second set of securing mechanisms.

15. The retention device of claim 7, wherein the securing mechanism is tine shaped.

16. The retention device of claim 7, wherein the securing mechanism is hook shaped.

17. An implantable lead for use with an implantable medical device (IMD), the lead comprising:

a lead body having a longitudinal axis extending between a proximal end and a distal end;
one or more electrodes disposed on the lead body;
one or more conductors coupled to the one or more electrodes;
a connector at the proximal end of the lead body for coupling to the IMD, the connector having one or more contacts corresponding to the one or more conductors; and
a retention device separate from the lead body, the retention device comprising:
  an elongate body including an outer surface, the elongate body defining a bore extending therethrough, the bore having a diameter sized to receive a portion of an implantable lead; and
  one or more securing mechanisms each having a first end coupled to the elongate body and a second end configured to push against tissue of the patient,
  wherein an entirety of each securing mechanism overlies a cylindrical portion of the elongate body;
  wherein the one or more securing mechanisms are configured to move from a pre-deployed compressed state to an expanded deployed state;
  wherein the outer surface of the elongate body includes a recess configured to receive a suture to secure the retention device on the lead, the lead configured such that tightening the suture while a lead is disposed within the bore reduces the diameter of the bore to secure the elongate body onto the lead; and
  wherein the outer surface of the elongate body has a receiving region of lesser diameter than another region of the outer surface of the elongate body such the when the securing mechanism is in the pre-deployed, compressed state, the receiving region allows the securing mechanism to be compressed therein such that the securing mechanism does not lie outside a largest diameter of the outer surface.

* * * * *